United States Patent
Zhu et al.

(10) Patent No.: US 9,876,537 B2
(45) Date of Patent: *Jan. 23, 2018

(54) PHASE CONTROLLED ARRAY FOR WIRELESSLY POWERING IMPLANTABLE DEVICES

(71) Applicant: Verily Life Sciences LLC, Mountain View, CA (US)

(72) Inventors: Jiang Zhu, Cupertino, CA (US); Sean Korhummel, San Carlos, CA (US); Stephen O'Driscoll, San Francisco, CA (US); You Zou, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/499,486

(22) Filed: Apr. 27, 2017

(65) Prior Publication Data

US 2017/0230084 A1    Aug. 10, 2017

Related U.S. Application Data

(63) Continuation of application No. 15/012,233, filed on Feb. 1, 2016, now Pat. No. 9,672,393.

(51) Int. Cl.
*H04B 5/00* (2006.01)
*A61B 5/00* (2006.01)
*A61B 5/07* (2006.01)

(52) U.S. Cl.
CPC ........... *H04B 5/0087* (2013.01); *A61B 5/002* (2013.01); *A61B 5/0031* (2013.01); *A61B 5/07* (2013.01); *H04B 5/0031* (2013.01)

(58) Field of Classification Search
USPC .................. 600/306, 375, 383; 607/60, 137; 235/375, 383
See application file for complete search history.

(56) References Cited

U.S. PATENT DOCUMENTS

| 5,935,078 A | 8/1999 | Feierbach |
| 9,055,917 B2 | 6/2015 | Mann et al. |

(Continued)

FOREIGN PATENT DOCUMENTS

| WO | 2009115102 A1 | 9/2009 |
| WO | 2010042054 A1 | 4/2010 |

(Continued)

OTHER PUBLICATIONS

Search Report and Written Opinion for PCT/US2016/069426 dated Apr. 20, 2017.

*Primary Examiner* — Allyson Trail
(74) *Attorney, Agent, or Firm* — McDonnell, Boehnen, Hulbert & Berghoff LLP

(57) ABSTRACT

A reader device includes an array of antenna coils configured to electromagnetically couple with devices implanted beneath or within skin of a human body. An implanted device can include a loop antenna or other means configured to couple with at least one antenna coil of the reader device to receive radio frequency energy from the reader device. The antenna coil array is configured to mount to the skin surface to improve the coupling between the implanted device and coils of the array. Further, the reader device is configured to select two or more antenna coils of the array and to operate the selected antenna coils to emit radio frequency power at respective amplitudes and relative phases to provide radio frequency power to the implanted device while increasing efficiency of the power transfer and reducing the exposure of the skin to radio frequency energy.

20 Claims, 8 Drawing Sheets

(56) References Cited

U.S. PATENT DOCUMENTS

| | | |
|---|---|---|
| 2004/0147969 A1 | 7/2004 | Mann et al. |
| 2008/0096495 A1 | 4/2008 | Shen |
| 2010/0280568 A1 | 11/2010 | Bulkes et al. |
| 2010/0298720 A1 | 11/2010 | Potkay |
| 2011/0087306 A1 | 4/2011 | Goossen |
| 2013/0041235 A1 | 2/2013 | Rogers et al. |
| 2014/0275916 A1 | 9/2014 | Nabutovsky et al. |
| 2014/0371824 A1 | 12/2014 | Mashiach et al. |
| 2015/0025613 A1 | 1/2015 | Nyberg et al. |
| 2015/0065837 A1 | 3/2015 | Abreu |
| 2016/0346537 A1 | 12/2016 | Mashiach |

FOREIGN PATENT DOCUMENTS

| | | |
|---|---|---|
| WO | 2011046674 A1 | 4/2011 |
| WO | 2015092747 | 6/2015 |

PHASE CONTROLLED ARRAY FOR WIRELESSLY POWERING IMPLANTABLE DEVICES

CROSS-REFERENCE TO RELATED APPLICATION

This application claims the benefit of and incorporates by reference the content of U.S. patent application Ser. No. 15/012,233, filed Feb. 1, 2016.

BACKGROUND

Unless otherwise indicated herein, the materials described in this section are not prior art to the claims in this application and are not admitted to be prior art by inclusion in this section.

Certain medical conditions or states can be characterized by values and/or changes over time of a physiological property (e.g., a flow rate and/or amount of blood in a portion of vasculature, an oxygen saturation of blood, a blood pressure). Such physiological properties can be measured by a device located outside the body. Additionally or alternatively, an implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a Bluetooth antenna and transmitter).

SUMMARY

Some embodiments of the present disclosure provide a device including: (i) an array of antenna coils that can be mounted proximate a skin surface and to span a specified area of the skin surface when so mounted, such that each antenna coil of the array of antenna coils has a respective degree of electromagnetic coupling with an antenna of an implanted device that is implanted beneath the skin surface; and (ii) a controller that is operably coupled to the array of antenna coils and that includes a computing device programmed to perform operations. The operations include: (1) determining a location, relative to the array of antenna coils, of the implanted device; (2) selecting, based on the determined location of the implanted device, two or more antenna coils of the array of antenna coils; (3) determining, based on the determined location of the implanted device, an amplitude and a relative phase for each of the selected two or more antenna coils; and (4) operating the selected two or more antenna coils to provide radio frequency power to the implanted device. Operating the selected two or more antenna coils to provide radio frequency power includes emitting from each of the selected two or more antenna coils radio frequency power according to a corresponding determined amplitude and relative phase.

Some embodiments of the present disclosure provide a method including: (i) determining a location of an implanted device relative to an array of antenna coils in a reader device mounted to a skin surface, wherein the array of antenna coils spans a specified area of the skin surface, wherein the implanted device is implanted beneath the skin surface, and wherein each antenna coil of the array of antenna coils has a respective degree of electromagnetic coupling with an antenna of the implanted device. The method additionally includes: (ii) selecting, based on the determined location of the implanted device, two or more antenna coils of the array of antenna coils; (iii) determining, based on the determined location of the implanted device, an amplitude and a relative phase for each of the selected two or more antenna coils; and (iv) providing, via the selected two or more antenna coils, radio frequency power to the implanted device, wherein providing radio frequency power to the implanted device comprises emitting from each of the selected two or more antenna coils radio frequency power according to a corresponding determined amplitude and relative phase.

These as well as other aspects, advantages, and alternatives, will become apparent to those of ordinary skill in the art by reading the following detailed description, with reference where appropriate to the accompanying drawings.

DETAILED DESCRIPTION

Figure 1A:
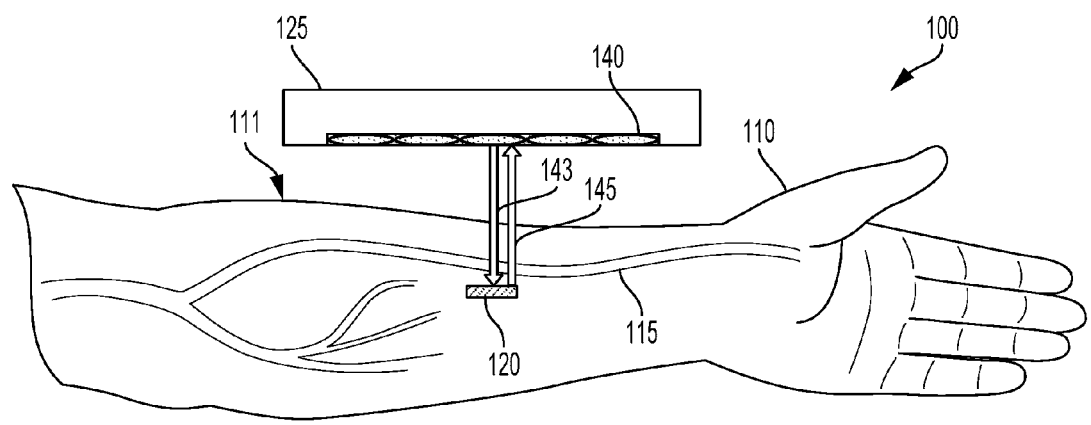
FIG. 1A is a cross-sectional view of an example reader device disposed proximate an arm and an example microelectronic device that is implanted beneath a skin surface of the arm and that is in communication with the reader device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Some embodiments of the present disclosure provide a reader device configured to be placed in contact with or otherwise mounted to a skin surface of a living body (e.g., to skin of the upper arm or abdomen of a person) and to interact with one or more devices implanted within and/or beneath the skin. Such implanted devices could each include one or more sensors configured to detect variables of the body, e.g., to detect variables related to hemodynamic properties of vasculature and/or blood in the skin. For example, the reader device could include one or more antenna coils that are operable to emit electromagnetic energy to power the implanted device via an antenna of the implanted device. Such electromagnetically coupled antenna coils could additionally be used to transmit and/or receive wireless communications from the implanted device (e.g., by detecting a pattern over time in an amount of radio frequency energy that is reflected and/or backscattered by the implanted device, by modulating an amplitude, phase, frequency, or other properties of the electromagnetic energy emitted to power to the implanted device). These electromagnetic interactions between the implanted device and the antenna coils could be achieved in the near field of the antenna coils, and properties of the antenna coils and/or of their operation could be specified to improve such near field interactions (e.g., by reducing an amount of electromagnetic energy radiated into the far field of the antenna coils). The reader device may additionally or alternatively be configured to communicate with implanted devices optically or through some other means.

A degree of electromagnetic coupling between an antenna (e.g., an antenna coil) of an implanted device and an antenna coil of a reader device could be related to a variety of factors. Such factors can include the orientation and location of the antenna coil relative to the antenna of the implanted device. To accommodate powering of implanted devices across a range of relative locations and/or orientations, the reader device can include an array of antenna coils that can be mounted proximate to a skin surface beneath which the implanted device is implanted. Each antenna coil of such an array of antenna coils could have a respective degree of electromagnetic coupling with the implanted device that is related to the respective location and/or orientation of each antenna coil relative to an antenna of the implanted device. Correspondingly, each of the antenna coils could have a respective efficiency of near-field electromagnetic power transfer to the implanted device, strength of a received near-field wireless transmission from the implanted device, or some other property of the interaction with the implanted device within the near-field region of one or more of the antenna coils.

In such examples, a particular antenna coil of the array of antenna coils could be selected and used to interact with the implanted device (e.g., to non-radiatively provide radio frequency energy to the implanted device, to receive/transmit near-field wireless transmissions from/to the implanted device). However, for some relative locations and/or orientations of an implanted device (e.g., when the implanted device is located on the edge of a coil, or between two or more coils of an array of antenna coils), it could be beneficial to operate multiple coils to provide power to the implanted device. For example, power transmitted from a single antenna coil, via near-field electromagnetic coupling between the single antenna coil and an antenna of the implanted device, could be insufficient to operate the implanted device, the efficiency of the power transfer could be low, and/or the amount of radio frequency energy that is emitted from the single antenna coil and absorbed by the skin when operating the single antenna coil to power the implanted device could be higher than some specified maximum value.

In such examples, two or more antenna coils could be operated to provide power to the implanted device. The amplitude and/or relative phase of the radio frequency power provided via each of the two or more antenna coils (that is, an amplitude and/or relative phase of radio-frequency sinusoidal or otherwise periodic signals applied to the two or more antenna coils) could be controlled to provide an increased amount of radio frequency power to the implanted device, to reduce an amount of radio-frequency energy absorbed by the skin (e.g., a total amount, a maximum amount per unit volume or area), or according to some other consideration. The identity of the selected two or more coils and/or the amplitude and relative phase of the radio frequency power delivered via each of the selected coils could be determined based on a detected location and/or orientation of the implanted device, relative to the array of antenna coils. Such a determination could be performed, by the reader device, by applying the location and/or orientation to select, from a lookup table, a set of coils and an amplitude and relative phase for the selected coils. Additionally or alternatively, an amount of radio frequency power received by the implanted device over time (e.g., an amount of power measured by the implanted device and wirelessly indicated to the reader device) could be used to adjust the identity of the selected coils and/or the amplitude and relative phase of the power emitted from the selected coils (e.g., using one or more feedback controllers). Other methods for selecting two or more coils and/or determining amplitudes and relative phases for such selected coils are anticipated.

The location and/or orientation of an implanted device relative to a reader device could be determined in a variety of ways. Determination of the relative location of the implanted device could include operating a camera or other light detecting means of the reader device, e.g., to detect an emitted and/or reflected light from the implanted device. In another example, the antenna coils could be operated to detect a degree of electromagnetic coupling and/or interaction between each of the antenna coils and the implanted device. In a further example, each of the antenna coils could be used, over time, to emit radio frequency power and the implanted device could, responsively, measure an amount of power received by the implanted device from each of the antenna coils and provide wireless indications of the measured amounts of power. The location and/or orientation of the implanted device could then be determined based on the wireless indications.

The antenna coils of the reader device could be operated in different ways. In some examples, each antenna coil could be coupled to a respective radio frequency transmitter and/or receiver (configured, e.g., to transmit radio frequency power and/or signals and to receive radio frequency signals, respectively). Alternatively, two or more of the antenna coils could be coupled to a single radio frequency transmitter and/or receiver, e.g., via a radio frequency switch. Such a radio frequency switch could be configured to electrically couple selected antenna coil(s) to one or more oscillators, amplifiers, envelope detectors, demodulators, level shifters, filters, or other components of a radio frequency transmitter and/or receiver. Further, such a radio frequency switch could be configured to couple non-selected antenna coils to a specified high impedance or a specified low impedance such that the non-selected antenna coils do not interfere with the electromagnetic coupling between and/or interaction of the selected antenna coil(s) and the implanted device.

Implanted and/or implantable devices as described herein could include a variety of sensors configured to detect a variety of physiological properties and/or properties of the environment of the implanted devices. In some examples, the sensor could include a light sensor, a pressure sensor, a strain sensor, an accelerometer, a biopotential sensor, a temperature sensor, an electrochemical sensor or some other sensor configured to detect an analyte, or some other sensor configured to detect one or more physical variables (e.g., a pressure, a displacement, a transmitted light intensity) related to hemodynamic properties of a human body, e.g., blood flow rates, blood flow velocities, pulse rates, pulse timings, blood pressures, blood oxygen saturation, pulse transit times, or other hemodynamic properties of blood, of portions of vasculature, of a heart, and/or of some other elements of the cardiovascular system of a body in which the implanted device is implanted. For example, an implanted device could be implanted proximate a portion of subsurface vasculature within skin beneath a surface of which the implanted device is located. In some examples, the implanted device could include one or more light detectors configured to detect an intensity (or other property) of light that is transmitted from outside the skin, through the portion of subsurface vasculature, to the light detector. Such a detected intensity could be related to a volume of blood in the portion of subsurface vasculature and could be used to determine a pulse rate, blood pressure, pulse transit time, or other hemodynamic properties of the portion of subsurface vasculature and/or of blood therein. Further, the reader device could include a light emitter configured to provide such light transmitted from outside the skin surface.

Note that reader devices, implanted/implantable devices, and other devices, systems, and methods described herein may be provided in devices that could be mounted on, proximate to, and/or within a variety of portions of the human body to measure a variety of physiological and/or hemodynamic properties of the human body (e.g., concentrations of a variety of analytes in a variety of fluids of the body, temperature, galvanic properties, ECG, muscle activity, blood flow rate, blood flow velocity, blood pressure, blood oxygenation, pulse transit time). Further, note that the implantable devices described herein may be provided in devices that could be implanted or otherwise located in locations other than locations within skin of a human body, e.g., locations in some other tissue of a human body, locations in an animal body, locations that are part of a natural or artificial environment. Correspondingly, reader devices described herein could be configured to be mounted on and/or proximate to the locations of such implanted devices and to electromagnetically power, communicate with, or otherwise interact with such implanted devices. It should be understood that the above embodiments, and other embodiments described herein, are provided for explanatory purposes, and are not intended to be limiting.

II. Example Reader Device

In a variety of applications, it can be beneficial to place a sensor in an environment of interest, e.g., to implant an implantable sensing platform within tissue of a person to detect physiological and/or hemodynamic parameters of the person. Placing a sensor in an environment of interest can allow for detection of a property of interest, e.g., improved detection of a pulse rate, a blood flow rate, an optical or other property of blood or other tissue, a concentration of an analyte in a fluid, or some other parameters of a person, e.g., of a portion of subsurface vasculature and/or of blood therein. For example, a sensor configured to detect one or more hemodynamic parameters and/or physical variables related thereto could be placed proximate a portion of subsurface vasculature. Such improved detection could be related to a reduced distance between a sensor and a target of interest, a reduced amount of tissue or other material intervening between a sensor and a target of interest, an increased stability of the interface between a sensor and the environment of a target of interest (e.g., a reduction of relative motion between the sensor and the target due to emplacement of the sensor proximate the target within an environment that also contains the target), or other factors.

Such a sensor implanted within a human body (e.g., beneath a skin surface, proximate a portion of subsurface vasculature) could be configured in a variety of ways. In some examples, a sensor could be part of an implanted device that is configured to wirelessly communicate with (e.g., to transmit sensor readings), receive energy from, or otherwise interact with other devices (e.g., reader devices configured to communicate with, provide power to, or otherwise interact with the implanted device) through a skin surface beneath which the implanted device is implanted. Such interaction could include the transmission and/or reception of optical energy, radio frequency energy, or other energies or fields that are able to be transmitted through intervening tissue (e.g., through the skin surface). For example, the implanted device could include an antenna (e.g., a loop of wire or coil) configured to electromagnetically couple with one or more corresponding antenna coils of a reader device.

Such electromagnetic coupling can allow electromagnetic fields generated by one of the reader device or the implanted device (e.g., by driving the antenna coil or antenna, respectively, with a time-varying voltage and/or current) to be received by the opposite device. For example, the reader device could operate the antenna coil(s) to provide wireless power to the implanted device, to transmit a wireless transmission to the implanted device, to receive a wireless transmission from the implanted device, or to otherwise interact with the implanted device via electromagnetic interactions in the near field of the antenna coil(s) of the reader device. Conversely, the implanted device could operate the antenna to transmit a wireless transmission to the reader device (e.g., by backscattering, reflecting, or otherwise modifying radio frequency power or fields provided by the reader device), to receive a wireless transmission from the reader device, or to otherwise interact with the reader device.

As an illustrative example, FIG. 1A shows, in cross-section, an arm 110 containing a portion of subsurface vasculature 115 located beneath a skin surface 111. An implanted device 120 is implanted beneath the skin surface 111 (e.g., at a depth beneath the skin surface 111 between approximately 1 millimeter and approximately 5 millimeters) such that the portion of subsurface vasculature 115 is positioned between the microelectronic device 120 and the skin surface 111. The portion of subsurface vasculature 115 could be an artery, a vein, a capillary, or some other portion of vasculature beneath the skin surface 111. The portion of subsurface vasculature 115 could be part of a capillary bed within the skin. A reader device 125 is located outside the skin surface 111 proximate the arm 110. The reader device 125 includes an array of antenna coils 140 that are each configured to have a degree of electromagnetic coupling with an antenna (not shown) of the implanted device 125.

Such electromagnetic coupling can be related to the location and/or orientation of each of the antenna coils of the array 140 relative to the antenna of the implanted device 120, the composition or geometry of tissues of the arm proximate the devices 120, 125, or other factors.

Note that the illustration of an implanted device that is implanted proximate to a portion of subsurface vasculature is intended as a non-limiting example. Implanted devices as described herein could be located proximate to a variety of different elements of a body (e.g., nerves, tendons, muscle fibers, bones, organs) to detect properties of such different elements of the body. In some examples, an implanted device could be implanted proximate a tendon and could detect motion of the tendon. This could include detecting a change in a pattern of constructive and destructive interference in light received from the tendon, e.g., light scattered by, reflected by, or otherwise emitted from the tendon in response to illumination (e.g., illumination by coherent light from outside a skin surface proximate the tendon). In some examples, an implanted device could be implanted proximate a nerve or muscle fiber and could detect electrical activity (e.g., action potentials) of the nerve or muscle fiber. This could include detecting electrical fields or currents produced by the nerve or muscle fiber, e.g., by detecting a biopotential between two or more electrodes of the microelectronic device. Implanted devices as described herein could be disposed within or proximate to other tissues and configured to detect other physiological parameters and/or physical variables, or could be disposed within environments that are not part of a human body.

Further, while the reader device 125 of FIG. 1A is illustrated as being located away from the surface of the arm 111, a reader device as described herein could be configured to be placed in contact with a skin surface beneath which an implanted device is located, or in contact with the surface of some other environment or material containing a wireless sensor device as described herein.

The implanted device 120 can be configured to detect physiological and/or hemodynamic parameters of the arm 110 (e.g., a hemodynamic parameter of the portion of subsurface vasculature 115 and/or of blood therein), to detect some other properties, or to provide some other functions. Related to such operations of the implanted device 120, the reader device 125 is configured to provide (using one or more antenna coils of the array of antenna coils 140) radio frequency power 143 to the implanted device 120. The reader device 125 is also configured to receive wireless transmissions 145 from the implanted device 120. In examples wherein the wireless transmissions 145 include radio frequency wireless transmissions, the reader device 125 could operate one or more antennas coils of the array of antenna coils 140 to receive the wireless transmissions 145. Additionally or alternatively, the wireless transmissions 145 could include optical signals (e.g., visible, infrared, or ultraviolet light emitted from the implanted device 120 over time to indicate information), and the reader device 125 could include one or more light sensors (e.g., photodiodes, phototransistors, cameras) that are operable to receive such optical signals.

The implanted device 120 can use radio frequency power provided by the reader device 125 to, e.g., operate a sensor to detect a physiological parameter (e.g., a hemodynamic parameter of the portion of subsurface vasculature 115), provide the wireless transmission 145 related to such detected parameters or other information to the reader device 125, or perform some other operations. The reader device 125 could be configured to operate the array of antenna coils 140 to provide some further functions, e.g., to transmit wireless transmissions to the implanted device 120 (e.g., by modulating a frequency, phase, amplitude, or other properties of the provided radio frequency power 143), to detect the location and/or orientation of the implanted device 120 relative to the reader device 125, or to provide some other functions.

The implanted device 120 could include one or more antennas, coils, waveguides, ferrites, striplines, or other components configured to receive the provided radio frequency power 143 (e.g., to receive radio frequency power at a specified frequency). Such energy-receiving elements could be configured to provide further functions, e.g., to receive wireless transmissions from the reader device 125 (e.g., by detecting time-varying patterns in amplitude, phase, frequency, or other properties of the received radio frequency energy), to detect a time-varying magnetic field (e.g., variations in the detected direction and/or magnitude of the Earth's magnetic field as the implanted device 120 is translated and/or rotated with motions of the arm 110), to provide radio-frequency wireless transmissions 145 to the reader device 125, or to provide some other functions according to an application. The implanted device 120 could additionally be powered by some other element(s) and/or sources of energy, e.g., an electrochemical battery (e.g., a zinc-oxygen battery), a capacitor, or some other energy storage means that could be charged or otherwise configured to include a store of energy before implanting the implanted device 120 in a body (e.g., beneath skin surface 111). In some examples, the implanted device 120 could be configured to receive chemical energy from the environment of the implanted device 120. In further examples, the implanted device 120 could be configured to receive optical power, e.g., from ambient light sources, from a light emitter of reader device 125, or from some other source.

The wireless transmission 145 includes a time-varying electromagnetic field (e.g., a radio frequency signal) emitted by the implanted device 120. An intensity, frequency, phase, direction or degree of polarization, or some other property of the emitted electromagnetic field could be controlled by the implanted device 120 in a manner related to information to be indicated, e.g., to provide an amplitude, phase, frequency, or otherwise-modulated carrier wave encoded to represent digital codes, binary values, or other information related to physical properties detected by one or more sensors of the implanted device, an operational state of the implanted device 120 (e.g., an amount of energy being received by the device 120), a cryptographic key or other user credential, or some other information. The emitted electromagnetic field could be generated by a coil, stripline, antenna, or other elements of the implanted device 120; additionally or alternatively, the emitted electromagnetic field could include electromagnetic energy received by the implanted device 120 and reflected by a coil, antenna, or some other element(s) of the implanted device 120 that has a controllable impedance or some other controllable electrical property. For example, an impedance could be selectively applied to terminals of a coil (or other antenna element(s)) to detune the coil such that the coil backscatters or otherwise reflects more or less received electromagnetic energy over time to indicate some information.

In some examples, the implanted device 120 could be configured to operate independently to log a plurality of values of a detected physical variable and/or hemodynamic or physiological parameter (powered, e.g., by ambient energy sources, by a battery, by glucose or some other source of biochemical energy in the body, or by some other power source) and subsequently to provide wireless transmissions 145 indicating such logged information, e.g., to the reader device 125. Additionally or alternatively, the implanted device 120 could be configured to operate in response to receiving radio frequency power 143 from the reader device 125 and to wirelessly transmit, to the reader device 125, information related to detected physical variables, hemodynamic or physiological parameters, or some other information. In some examples, detecting a hemodynamic or physiological property (e.g., a volume of blood in the portion of subsurface vasculature 115) could include detecting an interaction between the portion of subsurface vasculature 115 and/or arm 110 and the reader device 125, e.g., detecting an amount of absorption, by the portion of subsurface vasculature 115, of illumination provided by a light emitter of the reader device 125.

As illustrated in FIG. 1A, the reader device 125 is operating a particular antenna coil of the array of antenna coils 140 to interact with (i.e., to provide radio frequency power 143 to and to receive wireless transmissions 145 from) the implanted device 120. The reader device 125 could select and operate any of the antenna coils of the array of antenna coils 140 to perform such functions, or additional functions (e.g., to transmit wireless transmissions to the implanted device 120, to detect the depth of the implanted device 120 beneath the surface of the skin 111). Additionally or alternatively, more than one antenna coil of the array 140 could be operated (e.g., as a phased array to form a beam or other pattern of emitted electromagnetic energy) to provide wireless energy to, to provide wireless transmissions to, to receive wireless transmissions from, or to otherwise wirelessly interact with the implanted device 120. Further, multiple implanted devices could be disposed within the arm 110 (or some other environment of interest) and the reader device 125 could operate multiple antenna coils and/or multiple sets of antenna coils of the array 140 to interact with (e.g., to provide wireless energy to, to receive wireless transmissions from) multiple respective implanted devices.

Figure 1B:
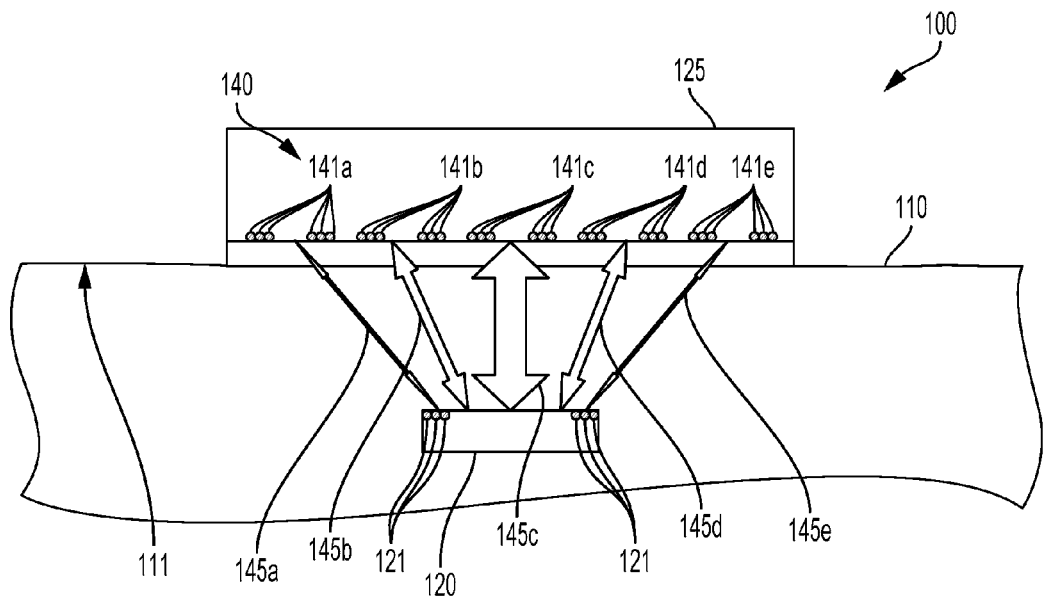
FIG. 1B is a cross-sectional view of the example reader device shown in FIG. 1A when mounted to the skin surface of the arm with illustration of the degree of electromagnetic coupling between an antenna of the implanted device and antenna coils of the reader device.

Each antenna coil of the array 140 has a respective degree of electromagnetic coupling with the antenna of the implanted device 120. To illustrate this, FIG. 1B shows the reader device 125 mounted to (e.g., held in place against by hand, strapped to, adhered to with an adhesive, or otherwise placed in contact with) the skin surface 111 of the arm 110. Five particular antenna coils 141*a-e* of the array of antenna coils 140 are shown in cross-section. Further, the antenna 121 of the implanted device 120 is shown in cross-section (illustrated, by way of example, as a loop antenna). The degree of electromagnetic coupling between each of the particular antenna coils 141*a-e* is illustrated by the thickness of respective arrows. Further, each antenna coil of the array 140 has a respective field geometry of any electromagnetic fields that may be generated using the antenna coil, e.g., by applying time-varying currents and/or voltages to the antenna coil. These field geometries can be related to the electrical properties of tissues or objects in the environment of the coils, e.g., by tissues or fluids of the skin or by the electrical properties of other coils of the array 140. Each antenna coil may also, when operated to transmit radio frequency power, provide radio frequency power to tissues or fluids of the skin 110. The amount of this power absorbed by the skin and the distribution across space of such absorption within the skin can be related to the geometry of the electromagnetic field generated by the antenna coils.

The degree of electromagnetic coupling (e.g., near-field electromagnetic coupling) between a particular antenna coil and the antenna 121 of the implanted device 120 can be related to a location or orientation of the implanted device 120 relative to the particular antenna coil, to properties of the environment of the antenna 121 and coils, or to some other factors. For example, the degree of electromagnetic coupling could decrease with increasing distance between the implanted device antenna 121. The degree of electromagnetic coupling could additionally be related to the degree of alignment (e.g., a relative angle between a characteristic axis of the implanted device antenna 121 and an antenna coil of the array 140, e.g., an axis perpendicular to the plane of an antenna coil). This is illustrated in FIG. 1B by the thickness of arrows 145*a*, 145*e* corresponding to antenna coils 141*a*, 141*e* being less thick than arrows 145*b*, 145*d* corresponding to antenna coils 141*b*, 141*d*, which are in turn less thick and the arrow 145*c* corresponding to the middle antenna coil 141*c*. The degree of coupling could additionally be related to a permittivity, permeability, conductivity, dielectric constant, or other properties of material disposed between and/or proximate to the implanted device antenna 121 and antenna coils of the array 140.

As shown, the reader device 125 is configured to mount to the skin surface 111 to minimize the distance between the implanted device antenna 121 and antenna of the array of antenna coils 140. Further, a reader device and/or an array of antenna coils thereof could be flexible, could have a curved shape, or could be configured in some other way to minimize the distance between an antenna of an implanted device and antenna coils of the array of antenna coils.

To maximize the amount of radio frequency power received by the implanted device 120 from the reader device 125 and/or to increase the efficiency of such power transfer, the array and/or a particular one or more antenna coils thereof could be moved to minimize a distance between the implanted device antenna 121 and a particular antenna coil of the array 140. This could include operating a servo or other actuator to adjust the location of the array 140 and/or elements thereof. Additionally or alternatively, a user could adjust the location of the reader device 125 on the skin to align a particular antenna coil with the implanted device 120, e.g., responsive to an instructing indication provided by a display or other elements of the reader device 125. Alternatively, the array 140 could include a plurality of antenna coils (as shown) that span a specified area (e.g., a specified area of the skin surface 111, when the reader device 125 is mounted thereto) and one or more antenna coils of the array (e.g., 141*c*) could be selected. The selected antenna coil(s) could then be operated to provide wireless power to the implanted device 120.

Figure 1C:
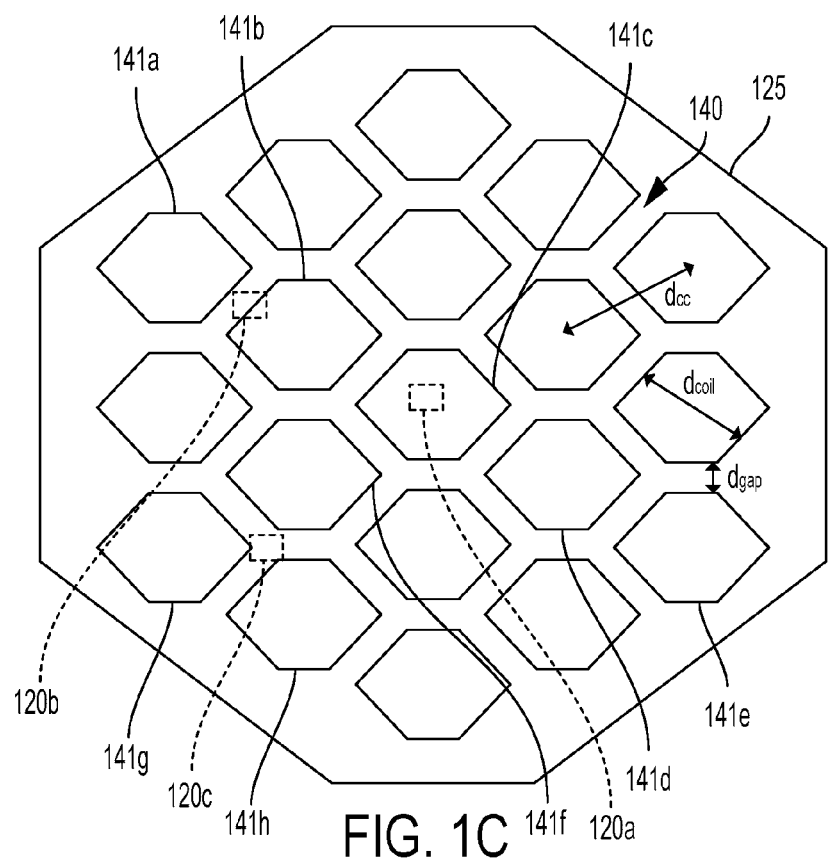
FIG. 1C is a schematic view of coils of an antenna array of the reader device shown in FIGS. 1A and 1B.

To illustrate this, FIG. 1C shows the arrangement of antenna coils (e.g., 141*a-h*) of the array of antenna coils 140 of the reader device. The location of a number of implanted devices 120*a*, 120*b*, 120*c* relative to the coils of the array 140 is also illustrated. Note that the sizes, shapes, and arrangements of antenna coils and the relative sizes and locations of the implanted devices 120*a*, 120*b*, 120*c*, are intended as a non-limiting example of the configuration of an array of antenna coils that spans a specified area, e.g., a specified area of a skin surface when mounted to such a skin surface.

In some examples, a single antenna coil of the array could be used to provide radio frequency power to an implanted device. For example, the electromagnetic coupling between a particular antenna coil and an implanted device could be greater than some specified amount, a particular antenna coil and an implanted device could be sufficiently aligned, or some other condition related to the location and/or orientation of an implanted device relative to a particular antenna coil could be satisfied such that the implanted device can be powered by radio frequency power provided by the particular coil. This is illustrated by way of example by the first implanted device 120a. As shown in FIG. 1C, the first implanted device 120a is located near the center of a first particular antenna coil 141c of the array of antenna coils 140. The first particular antenna coil 141c could be operated to transmit radio frequency power to the first implanted device 120a.

However, in some examples, the relative location and/or orientation of an implanted device could be such that it is beneficial to operate multiple antenna coils of the array 140 to provide radio frequency power to an implanted device. For example, the implanted device could be located at the edge of an antenna coil, between antenna coils, could have an orientation such the coupling between the implanted device and any one antenna coil is poor, or could be located or oriented in some other way such that it is beneficial to operate multiple antenna coils of the array 140 to transmit radio frequency power to the implanted device. In such examples, two or more antenna coils of the array 140 could be selected and each of the selected antenna coils could be operated to emit radio frequency power at a respective amplitude and relative phase.

For example, as shown in FIG. 1C, a second implanted device 120b is located at the edge of one of the coils 141b of the array 140 and near another coil 141a of the array. In such an example, the two nearby coils 141b, 141a could be operated to emit radio frequency power at respective amplitudes and relative phases to provide power to the second implanted device 120b. In another example, a third implanted device 120c is located between three coils 141f, 141g, 141h of the array 140. In this example, the three nearby coils 141f, 141g, 141h could be operated to emit radio frequency power at respective amplitudes and relative phases to provide power to the third implanted device 120c. The amplitudes and relative phases of the radio frequency power emitted from each of the selected antenna coils could be specified such that a target implanted device is located within a region of constructive interference, in the near field of the selected coils of the array 140, between the time-varying electromagnetic fields emitted from the selected coils of the array 140.

As shown in FIG. 1C, the antenna coils are hexagonal, have substantially the same size, are non-overlapping, and are arranged in a substantially regular, repeating pattern across the area spanned by the array 140. However, the antenna coils of an array of antenna coils of a reader device as described herein could be configured and/or arranged in some other way to span a specified array according to an application. For example, the antenna coils could be triangular, circular, square, elongate, or some other shape. Further, the antenna coils could partially overlap each other, could be arranged irregularly (that is, not in a substantially regular, repeating pattern). Further, while the illustrated array of antenna coils 140 includes antenna coils that are substantially planar and that are arranged in the array 140 such that the antenna coils are substantially coplanar, other orientations and/or arrangements of antenna coils are anticipated. For example, an array of antenna coils could include a plurality of antenna coils that have a variety of different orientations, e.g., to provide greater control over the geometry of a radio-frequency electromagnetic field generated by operating two or more antenna coils of the array 140 to provide radio frequency power at respective amplitudes and relative phases (e.g., to control a pattern of constructive and destructive interference between radio frequency power emitted from each of the operated two or more antenna coils).

Further, a size, impedance, or other properties of the antenna coils could be specified according to an application. For example, the antenna coils could have a size (indicated in FIG. 1C by the diameter $d_{coil}$) that is related to a frequency of radio frequency power provided, by the antenna coils, to an implanted device. Additionally or alternatively, such a size could be specified to maximize the degree of electromagnetic coupling between the antenna coil and an implanted device that is located at a specific depth beneath the skin. In a particular example, an antenna coil could have a diameter of between approximately 3 millimeters and approximately 3.5 millimeters in order to, for example, maximize the degree of electromagnetic coupling between the antenna coil in an implanted device located between approximately 1 millimeter and approximately 2 millimeters beneath the surface of the skin. The size of the antenna coil could be increased in order to maximize the degree of electromagnetic coupling with implanted devices located at greater depths within the skin. Correspondingly, a frequency of electromagnetic energy provided by the antenna coil(s) could be decreased. Antennas of an array of antenna coils could have respective different sizes or other respective different properties.

The distance between the antennas could be specified to minimize the degree of electromagnetic coupling between the antenna coils of the array, to maximize the area of the array that is within at least one antenna coil of the array (e.g., to minimize areas wherein the degree of electromagnetic coupling between a single antenna coil and an implanted device is low), or according to some other consideration. For example, the distance between windings of individual antenna coils of the array of antenna coils 140 (indicated in FIG. 1C by the distance $d_{gap}$) could be specified to minimize electromagnetic coupling between adjacent coils while also minimizing the area of the array 140 that is not covered by any of the antenna coils. In a particular example, distance between windings of individual antenna coils of the array of antenna coils 140, $d_{gap}$, could be approximately 0.5 millimeters. The distance between the centers of the antenna coils (indicated in FIG. 1C by the distance $d_{cc}$) could be specified based on this specified inter-antenna distance and on the size of the coils. For example, if $d_{gap}$ is approximately 0.5 millimeters and the size of the coils ($d_{coil}$) is between approximately 3 millimeters and approximately 3.5 millimeters, $d_{cc}$ could be between approximately 3.2 millimeters and approximately 3.7 millimeters.

The size, shape, and composition of antenna coils of an array of antenna coils or other properties of the configuration of an antenna coil array of a reader device could be specified according to a variety of considerations. Such considerations can include increasing an amount of radio frequency power that can be provided, via the antenna coils, to an implanted device, increasing an efficiency of radio frequency power transfer to the implanted device (e.g., by increasing a ratio of the amount of power received by the implanted device relative to the amount of power absorbed by tissues or fluids of the skin), decreasing a volume or area density of absorption of radio frequency power by tissues or fluids of the skin (e.g., by keeping the amount of power absorbed by any particular volume or area of the skin below some specified maximum, by increasing a ratio of the amount of power received by the implanted device relative to the maximum volume or area density of absorption of radio frequency power by tissues or fluids of the skin), or some other considerations.

According to these considerations, multiple antenna coils of the array could be operated simultaneously to provide radio frequency power, at respective amplitudes and relative phases. Additionally or alternatively, the array of antenna coils could be configured to increase a degree of electromagnetic coupling between antenna coils of the array and an antenna of an implanted device that is implanted beneath a skin surface. This can include minimizing the distance between the antenna coils and the implanted device and the reader device when the reader device is mounted to the skin surface, e.g., by configuring the reader device such that the antenna coils are in direct contact with the skin surface and/or such that the antenna coils are separated from the skin surface by a layer of protective or otherwise configured material having a specified small thickness.

Maximizing a degree of electromagnetic coupling between antenna coils of the array and the antenna of the implanted device can also include specifying a quality factor, a size, a resonant frequency, an impedance, a standing wave ratio, or some other properties of the antenna coils of the array. This can include coupling the antenna coils to respective capacitors, disposing a layer of material having a specified thickness, dielectric constant, or other properties between the antenna coils and the skin surface, e.g., to prevent detuning of the antenna coils or other effects on the electrical properties of the antenna coils by tissues of the skin. Maximizing a degree of electromagnetic coupling between antenna coils of the array and the antenna of the implanted device can include configuring the reader device according to further considerations.

Figure 2:
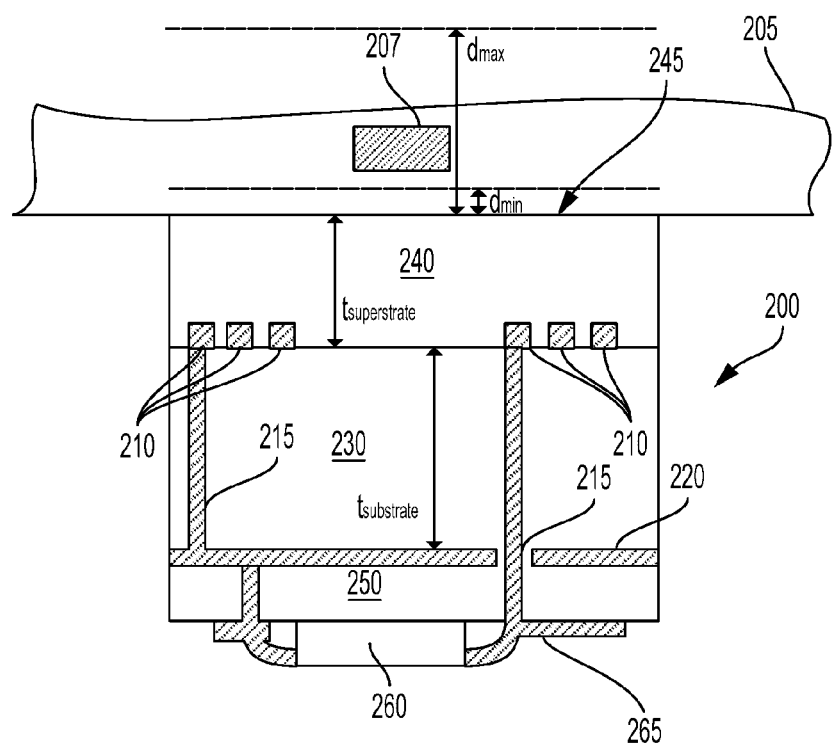
FIG. 2 is a cross-sectional schematic view of elements of an example reader device that is mounted to a skin surface of an arm and an example microelectronic device that is implanted beneath the skin surface of the arm and that is in communication with the reader device.

As an illustrative example, FIG. 2 illustrates, in cross-section, elements of a reader device 200, including the windings of a particular antenna coil 210 of an antenna array of the reader device 200. The reader device 200 is mounted to the surface of skin 205 proximate the location of an implanted device 207 within the skin. The implanted device 207 is located at a depth beneath the surface of the skin that is within a range of expected depths, indicated by $d_{min}$ and $d_{max}$. A mounting surface 245 of the reader device 200 is in contact with the skin 205. A contact layer 240 having a thickness $t_{superstrate}$ is disposed between the antenna coil 210 and the skin 205 and includes the mounting surface 245. The reader device 200 further includes a ground plane 220 that is separated from the antenna coil 210 by a spacing layer 230 having a thickness $t_{substrate}$. The reader device further includes a printed circuit board 250 (PCB) on which are disposed electronics 260. The electronics 260 are coupled, via traces 265 formed on the PCB 250, to the antenna coil 210, the ground plane 220, and other elements of the reader device 200 (not shown). Properties of the device 200 (e.g., a size or diameter of the coil 210, the thicknesses of the contact layer 240 and/or spacing layer 230) could be specified relative to the expected depth of the implanted device 207 beneath the skin (e.g., based on $d_{min}$ and $d_{max}$), the size of an antenna of the implanted device 207, or some other factors.

As shown, the antenna coil 210 is separated from the skin surface by a contact layer 240. The contact layer 240 could be configured to protect the antenna coil 210 from damage. The contact layer 240 could also have a thickness, dielectric constant, or other properties specified to prevent or reduce loading, detuning, or other effects of the skin 205 on electrical properties of the antenna coil 210. For example, the contact layer 210 could be composed of a low-loss material (e.g., a hydrocarbon/ceramic laminate material) to minimize dissipation of electromagnetic energy emitted by the coil 210. For example, the contact layer 240 could be composed of a material having a loss tangent that is less than approximately 0.002. Additionally or alternatively, contact layer 210 could have a low relative permittivity that is low, in order to maximize the efficiency of the antenna. For example, the contact layer could have a relative permittivity that is less than approximately 3.5.

In order to decrease detuning of the antenna coil 210 or other deleterious electrical effects of the skin 205 (e.g., of the relatively high relative permittivity or other electrical properties of the skin) on the performance of the antenna 210, the thickness of the contact layer 210 could be increased. However, increasing the thickness of the contact layer 240 could decrease coupling between the antenna coil 210 and the antenna of the implanted device 207 by increasing the distance between the implanted device 207 and the antenna coil 210. Thus, the thickness of the contact layer 240 could be specified based on a combination of factors (e.g., reducing distance to the implanted device 207 while minimizing the effects of the skin 205 on electrical properties of the antenna coil 210), e.g., the contact layer 240 could have a thickness between approximately 0.1 millimeters and approximately 0.4 millimeters. Alternatively, the contact layer 240 could be omitted from the reader device 200.

The illustrated reader device 200 includes a ground plane 220 separated from and substantially parallel to the antenna coil 210. The ground plane 220 could be composed of copper or some other conductive material. The ground plane 220 is separated from the antenna coil 210 by a spacing layer 230. The spacing layer could be composed of a low-loss material (e.g., having a loss tangent less than approximately 0.002) or otherwise specified (e.g., to have a low relative permittivity, e.g., less than approximately 3.5) to improve the electromagnetic coupling between the antenna coil 210 and the implanted device 207, to reduce an amount of energy emitted from the antenna coil 210 that is absorbed by the spacing layer 230, to increase an efficiency of the antenna coil 210, to minimize radiation of electromagnetic energy by vias 215 connecting the coil 210 to other elements of the device 200, or according to some other consideration.

The ground plane 220 and properties thereof (e.g., thickness, material composition, distance from the antenna coil 210) could be configured to increase the electromagnetic coupling between the antenna coil 210 and an antenna of the implanted device 207, e.g., by reflecting radio frequency waves emitted from the antenna 210 and/or the implanted device 207 (e.g., by being separated from the antenna coil 210 by a distance related to the wavelength of the emitted radio frequency waves and/or related to the size of the antenna coil 210). For example, if the diameter of the antenna coil 210 is between approximately 3 millimeters and approximately 3.5 millimeters, the ground plane could be greater than approximately 1.5 millimeters from the antenna coil 210 (that is, the spacing layer 230 thickness, $t_{substrate}$, could be greater than approximately 1.5 millimeters). The thickness of the spacing layer 230 could be increased with increases in the size of the antenna coil 210.

The ground plane could be formed to include a variety of structures, e.g., radio frequency resonators, reflectors, or other structures configured to improve transfer of radio frequency energy and/or transmissions between the antenna coil 210 and the implanted device 207. The reader device 200 could include additional ground plane layers and/or layers of formed resonators, reflectors, or other structures (e.g., disposed between the illustrated ground plane 220 and the antenna coil 210, disposed on the mounting surface 245 of and/or within the contact layer 240). Alternatively, the ground plane 220 could be omitted from the reader device 200.

The illustrated structures of the reader device 200 could be fabricated in a variety of ways. In some examples, the antenna coil 210, ground plane 220, and/or traces 265 could be formed via deposition, photo-patterning, or some other methods on a multi-layer printed circuit board. For example, the antenna coil 210 and ground plane 220 could be formed on opposite sides of a sheet of low-loss material and electrically and mechanically coupled to the PCB 250 on which the traces 265 are formed. In another example, the ground plane 220 and traces 265 could be formed on opposite sides of the PCB 250, and the spacing layer 230, antenna coil 210 (e.g., as one or more pieces of wire wound into a coil), and contact layer 240 could be disposed thereon. In a further example, the traces 265, PCB 250, ground plane 220, spacing layer 230, antenna coil 210, and contact layer 240 could be formed as a single multi-layer printed circuit board. In some examples, one or more of the illustrated structures could be a flexible material, such that an array of antenna coils that comprises the illustrated structures is flexible.

In some examples, one or more of the illustrated structures could be composed of a transparent material such that illumination can be delivered to the implanted device 207 and/or the skin 205 through such structures and/or such that light reflected by, scattered by, fluorescently absorbed and re-emitted by, or otherwise emitted by the implanted device 207 and/or skin 205 can be detected through such structures. Additionally or alternatively, a window could be formed through one or more of the illustrated structures to allow illumination to be emitted through such windows and/or to allow light to be received form the implanted device 207 and/or skin 205 through such windows.

III. Selection of Coils of an Array of Antenna Coils and Determination of Amplitudes and Relative Phases of Radio Frequency Power Emitted Therefrom As noted above, an array of antenna coils mounted to a skin surface can be operated in a variety of ways to provide radio frequency power to a device implanted beneath the skin surface. In some examples, e.g., wherein an electromagnetic coupling and/or alignment between a power-receiving antenna of the implanted device and a particular antenna coil of the array is particularly good, a single antenna coil of the array of antenna coils could be operated to emit radio frequency power to the implanted device. However, in some examples, two or more antenna coils of such an array could be operated to emit radio frequency power to wirelessly provide power to the implanted device. Two or more antenna coils could be used in such a way when a single coil in unable to provide sufficient power to the implanted device, e.g., when the implanted device is located far from the center of any of the antenna coils of the array and/or when the orientation of the antenna of the implanted device is not oriented in a manner that facilitates transmission of radio frequency power from any one antenna coil to the implanted device. Additionally or alternatively, two or more antenna coils could be used to provide power to an implanted device according to some other consideration, e.g., to increase an efficiency of power transfer, to reduce an amount of radio frequency power absorbed by tissue of the skin, to decrease a maximum amount of radio frequency power absorbed by a particular area or volume of the skin (e.g., to limit a maximum power absorption density), or according to some other consideration.

The selection of antenna coils of such an array of antenna coils, and the determination of amplitudes and relative phases of radio frequency power emitted from each of the selected antenna coils, could be determined based on the location and/or orientation of an implanted device relative to the array of antenna coils. A system including such an array of antenna coils could determine the relative location and/or orientation of an implanted device in a variety of ways. In some examples, the system could detect the location and/or orientation of the implanted device based on light emitted, scattered, and/or reflected by the implanted device. This could include operating one or more light sensors (e.g., photodiodes, cameras) of the device to receive light emitted, reflected, and/or scattered from the implanted device. This could further include the system illuminating the implanted device (e.g., with one or more LEDs, lasers, or other light-emitting elements). Additionally or alternatively, a system including such an array of antenna coils could operate the array of antenna coils to determine the relative location and/or orientation of an implanted device.

An array of antenna coils could be operated in a variety of ways to detect the location and/or orientation of an implanted device relative to the array of antenna coils. For example, the array could be operated to detect a degree of electromagnetic coupling between the implanted device and each of the antenna coils of the array. This could include providing, from each of the antenna coils in turn, radio frequency power to the implanted device. A signal strength of radio frequency signals scattered by, reflected from, or otherwise received from the implanted device by each antenna coil, in response to the antenna coil providing the radio frequency power (e.g., during a respective period of time), could be detected and used to determine the location and/or orientation of the implanted device. Additionally or alternatively, the implanted device could measure an amount of radio frequency power received from each of the antenna coils (e.g., during respective different periods of time) and could provide wireless transmissions indicative of the amount of radio frequency power received by the implanted device. This could include, e.g., measuring a magnitude of a voltage output from a radio frequency rectifier that is coupled to an antenna of the implanted device. Detected signal strengths, received wireless transmissions, or other information related to the location and/or orientation of the implanted device could be applied to a lookup table or used in some other way to determine a location and/or orientation of the implanted device relative to the array of antenna coils.

Based on a determined location and/or orientation of an implanted device relative to antenna coils of an array of antenna coils, a number of the antenna coils could be selected and operated to provide radio frequency power to the implanted device or to otherwise interact with the implanted device (e.g., to transmit radio frequency signals to the implanted device, to receive radio frequency signals from the implanted device). The coils could be selected, and properties of their operation specified (e.g., amplitudes and/or relative phases of emitted radio frequency power), according to a variety of considerations, e.g., to increase an amount of power received by the implanted device, to reduce an amount of power absorbed by skin or other tissues, to reduce a maximum amount of power absorbed by a particular volume or area of skin or other tissues (e.g., to maintain the maximum volume or area density of radio frequency power absorbed by the skin), or according to some other considerations. In some cases, this could include selecting a single antenna coil of the area and operating the selected single antenna coil to provide radio frequency power to an implanted device. For example, if the implanted device is located near the center of a particular antenna coil and/or if a characteristic direction of an antenna (e.g., a direction normal to a plane of a substantially planar antenna coil) of the implanted device is aligned with the particular antenna coil, the particular antenna coil could be selected from the array of antenna coils and singly operated to provide radio frequency power to the implanted device.

In other cases, two, three, or more antenna coils could be selected and operated to provide radio frequency power according to respective amplitudes and relative phases to the implanted device. For example, the implanted device could be located near the edge of a single coil, or between two or more coils, and the closest two, three, or more coils could be selected and operated to provide radio frequency power to the implanted device. The amplitudes and relative phases of the radio frequency power emitted from each of the selected antenna coils could be specified according to the considerations described herein, e.g., to increase an amount of power received by the implanted device, to increase an efficiency of power transfer to the implanted device, to reduce an amount and/or a density of power absorbed by the skin or other tissues, or according to some other considerations. This could include specifying the amplitudes and relative phases of the radio frequency power emitted from each of the selected antenna coils such that the near-field radio frequency fields generated by the antenna array exhibit a pattern of constructive and destructive interference within the skin. The amplitudes and relative phases could be specified such that the pattern of constructive and destructive interference satisfies some considerations, e.g., such that the location of an implanted device is within a region of constructive interference within the exhibited pattern of constructive and destructive interference and/or such that a direction of maximal radio frequency field intensity is aligned, at the location of the implanted device, with a characteristic direction of an antenna or other radio frequency power-receiving element(s) of the implanted device.

The selection of a set of antenna coils from an array of antenna coils to provide radio frequency power to an implanted device, and the determination of amplitudes and relative phases of such emitted radio frequency power in examples wherein two or more antenna coils are selected, could be determined, based on a location and/or orientation of the implanted device relative to the array of antenna coils, in a variety of ways. For example, a model of the electrical properties of the array of antenna coils, skin and other tissue, and the implanted device could be used to determine the identity of antenna coils to select and the amplitude and relative phase of the radio frequency power emitted via the selected antenna coils using a method of optimization. Such a method of optimization could include a genetic algorithm, dynamic programming, gradient descent, or some other methods or combinations of methods. The method used could operate to increase an amount of power received by the implanted device, to increase the efficiency of the power transfer, or according to some other considerations as described herein. Such optimizations could be performed by a controller of a device that includes the array of antenna coils. Additionally or alternatively, such optimizations could be performed for a range of different locations and/or orientations of an implanted device relative to an array of antenna coils and the optimizations could be used to determine information for one or more lookup tables that could be used to determine, based on a location and/or orientation of an implanted device, a set of antenna coils to use to provide radio frequency power and, in examples wherein two or more antenna coils are selected, an amplitude and relative phase of radio frequency power to emit from each of the selected antenna coils.

Additionally or alternatively, other methods and/or sources of information could be used to select antenna coils and/or to determine the amplitude and relative phases of radio frequency power emitted from such selected antenna coils. For example, the implanted device could measure an amount of radio frequency power received by the implanted device (e.g., by measuring a voltage output from a rectifier of the implanted device that is coupled to an antenna of the implanted device) from an array of antenna coils of a system and could transmit wireless indications (e.g., radio frequency signals, optical signal) to the system in response. The system could then, based on the received wireless indications of the amount of power received by the implanted device, select antenna coils of the antenna array and specify the amplitude and relative phase of radio frequency power emitted via the selected antenna coils. This could include using a genetic algorithm, operating one or more negative feedback loops, or operating in some other way, based on received wireless indications or other information related to an amount of radio frequency power received by an implanted device, to select antenna coils and to determine amplitudes and relative phases of radio frequency power emitted via the selected antenna coils. In some examples, a lookup table of other method could be used to initially, based on a location and/or orientation of an implanted device, select antenna coils and determine amplitudes and relative phases of radio frequency power emitted from the selected antenna coils. Subsequently, the identity of the selected coils and/or the amplitude or relative phase of the radio frequency power emitted from the selected coils could be changed based on received wireless indications or other information related to an amount of radio frequency power received by the implanted device.

IV. Example Implantable Microelectronic Device

Reader devices described herein include an array of antenna coils configured to provide wireless (e.g., radio frequency) energy to, to transmit wireless transmissions to, to receive wireless transmissions from, or other otherwise wirelessly interact with implanted devices. Such implanted devices could include one or more antennas (e.g., multi-turn coil antennas) configured to receive such wireless power, to communicate wirelessly with the reader device, or to perform some other functions. Such implanted devices could include a variety of electronics configured to provide such functions and/or to provide further functions, e.g., to operate a sensor (e.g., a light sensor, an accelerometer, a strain sensor, an analyte sensor, a biopotential sensor) of the implanted device to measure a property and to transmit a wireless transmission related to the measured property and/or related to some other information (e.g., information about the identity or operational state of the implanted device, information about a cryptographic key, information about a user profile or user authentication information).

Such implanted devices could have a very small size (e.g., could have a largest dimension that is less than approximately 1 millimeter). Thus, implanted devices as described herein could be described as microelectronic devices. Such microelectronic devices could include logic gates, microcontrollers, or other digital logic elements configured to be powered by wireless power received from a reader device and/or to generate wireless transmissions to the reader device. Alternatively, implanted devices as described herein could include only analog components (e.g., resonators, variable capacitors having a capacitance related to a physical variable of interest, surface acoustic wave transducers and/or filters). In some examples, components (e.g., electronics, sensors, antennas) of such implanted devices could be enclosed within a protective and/or encapsulating shell or layer, e.g., glass, a passivation layer formed on a semiconductor, to protect the components from the environment within a body and/or to improve the biocompatibility of the implanted device.

A microelectronic implanted device as described herein (e.g., 120, 207) could be formed by a variety of processes such that the microelectronic device has a small size (e.g., a largest dimension less than approximately 0.4 millimeters). In some examples, this could include forming most or all of the elements of the microelectronic device on or within a single integrated circuit (e.g., an integrated circuit having an area of less than approximately 400 microns by less than approximately 400 microns and a thickness less than approximately 100 microns). That is, a sensor, an energy receiver, a transmitter, a controller, and/or some other elements of the microelectronic device could be provided in a single integrated circuit. In some examples, additional components could be formed on and/or adhered or connected to such an integrated circuit. For example, a coil or other antenna structure(s) could be electrically connected to and/or wound around the periphery of such an integrated circuit. Further, a layer of protective, biocompatible, analyte-sensitive, or otherwise configured material could be formed on one or more surfaces of such an integrated circuit (e.g., to encapsulate the integrated circuit) to provide some other functions, e.g., to control an interface between the integrated circuit and tissue into which the integrated circuit is implanted or otherwise disposed. In some examples, a microelectronic device could be formed from multiple integrated circuits reflow-soldered, adhered with an adhesive, or otherwise bonded together (e.g., a first integrated circuit that includes a controller and a sensor bonded to a second integrated circuit that includes an energy receiver, a transmitter, and an antenna coil electronically connected to the energy receiver and transmitter).

Figure 3A:
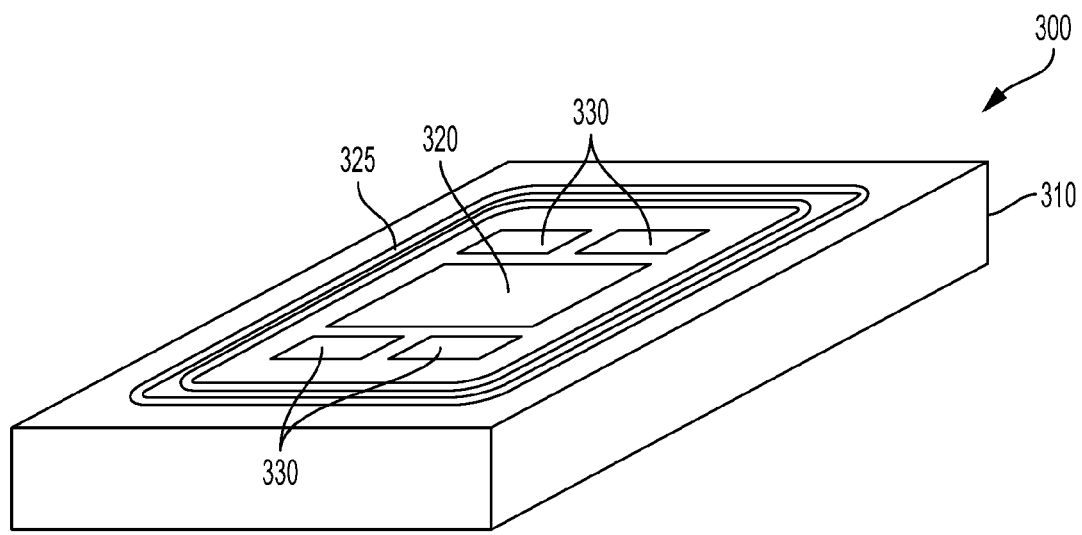
FIG. 3A is a perspective view of an example microelectronic device.
Figure 3B:
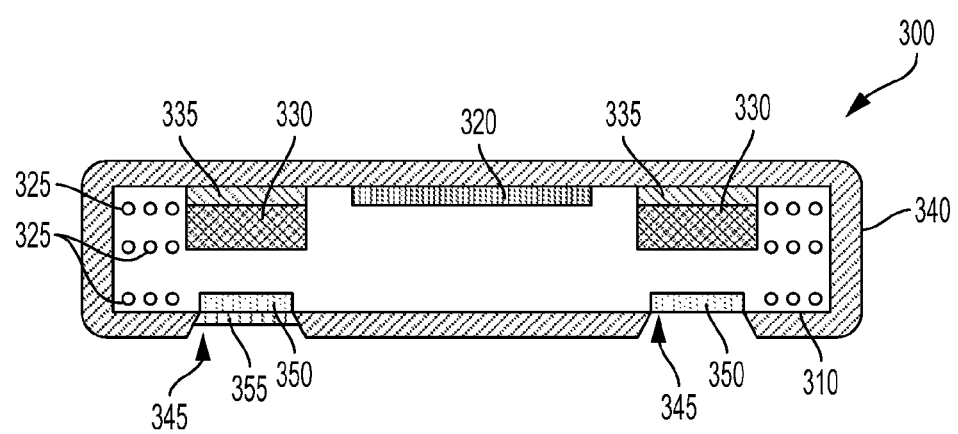
FIG. 3B is a cross-sectional view of the example microelectronic device shown in FIG. 3A.

As an illustrative example, FIGS. 3A and 3B show (in a perspective view and a cross-sectional view, respectively) an implantable microelectronic device 300 that comprises a single integrated circuit 310 (e.g., an integrated circuit formed from a single piece of silicon or some other semiconductor or other integrated circuit substrate material). A variety of components of the microelectronic device 300 are formed from the integrated circuit 310. These components include an antenna coil 325, a photovoltaic cell 320, a number of light sensors 330 (e.g., photodiodes, phototransistors, some other optoelectronic elements), and first and second electrodes 350. The microelectronic device 300 further includes, formed on the surface(s) of the integrated circuit 310, optical filters 335, an encapsulation layer 340, and an analyte-sensitive substance 355.

The coil 325 could be configured to receive wireless energy (e.g., radio frequency power transmitted from a reader device or other external system) to power the microelectronic device 300. Additionally or alternatively, the coil 325 could be configured to receive and/or transmit wireless transmissions from/to an external system or device (e.g., from/to one or more antenna coils of an array of antenna coils of a reader device as described elsewhere herein). The coil could be operated to emit wireless indications by controlling a pattern over time of an amount of received radio frequency power that is backscattered or otherwise reflected by the coil 325. This could include detuning the coil 325 or otherwise controlling one or more electrical properties of the coil 325, over time, by connecting a specified impedance to the coil 325 (e.g., by operating an electrical switch to connect a specified low or high impedance across two terminals of the coil 325). As shown, the coil 325 in includes multiple turns of conductive material (e.g., polysilicon, metallic traces, some other conductive material) formed in multiple layers. Alternatively, a coil could include a single turn formed in multiple layers (e.g., an effectively helical coil), a number of turns formed in a single layer (e.g., a spiral coil), and/or some other shape or configuration. Further, the microelectronic device 300 could include striplines, fractal antennas, patch antennas, or some other formed elements configured to transmit or receive wireless transmissions and/or to receive wireless energy to power the microelectronic device 300.

Additionally or alternatively, the microelectronic device 300 could include an LED, laser, or other optoelectronic element(s) (not shown) configured to provide optical wireless indications (e.g., by controlling a pattern over time of an intensity, wavelength, polarization degree or direction, or some other property of an emitted optical energy over time).

The photovoltaic cell 320 is configured to receive optical energy to power the microelectronic device 300. Further, the photovoltaic cell 320 could be used as a light sensor to detect an intensity or other property of light received by the photovoltaic cell 320 (e.g., to detect an intensity of light transmitted through a portion of subsurface vasculature and received by the photovoltaic cell 320). This could include detecting a current or voltage produced by the photovoltaic cell 320.

The light sensors 330 each include one or more of a photodiode, phototransistor, photoresistive element, or other light-sensitive element(s). The light sensors 330 can detect the intensity of light having a specified wavelength, polarization, direction of incidence, or some other property of light. In some examples, this could include light-sensitive elements of the light sensors 330 being sensitive to the intensity of received light and the optical filters 335 being configured to block light that has a wavelength, polarization direction, or other property that does not correspond to a specified range of wavelengths, polarization directions, or other properties such that the intensity detected by the light-sensitive elements corresponds to the intensity of light within the specified range of wavelengths, polarization directions, or other properties. For example, the optical filters 335 could include Bragg reflectors, color filters, or other elements configured to pass light within a specified range of wavelengths. In another example, the optical filters 335 could include gratings or other elements configured to pass light that is incident from within a specified range of angles relative to the microelectronic device.

As shown, the microelectronic device 300 includes a number of different light sensors 330. The light sensors 330 could be configured to detect substantially the same property of light (e.g., the intensity of received light within a specified range of wavelengths from substantially the same range of incident angles relative to the microelectronic device 300) that is received at different locations of the microelectronic device (e.g., locations corresponding to the locations of the light sensors 330). In such examples, the outputs of the different light sensors 330 could be used to map the intensity of light across a surface of the microelectronic device 300, to determine a gradient of the light intensity, to determine a relative absorption of light by a portion of subsurface vasculature proximate the microelectronic device 300 (e.g., by comparing the intensity of light received by a light sensor 330 beneath the portion of subsurface vasculature to the intensity of light received by a light sensor 330 that is not beneath the portion of subsurface vasculature), or to perform some other determination or function. Additionally or alternatively, different lights sensors 330 could be configured to detect light within different ranges of wavelengths, from different incident directions, or that differs according to some other property. For example, a first light sensor 330 could be configured to detect light of a first wavelength (e.g., a red wavelength) that is transmitted through a portion of subsurface vasculature and a second light sensor 330 could be configured to detect light of a second wavelength (e.g., a near-infrared wavelength) that is transmitted through the portion of subsurface vasculature and an oxygen content or saturation of the blood in the portion of subsurface vasculature could be determined based on the intensity of light detected by the first and second light sensors 330.

The first and second electrodes 350 could be configured and/or operated in a variety of ways to provide detection of biopotentials (e.g., voltages and/or currents related to an electromyogram, an electrocardiogram, or signals related to other electrically active cells of a body), to detect the concentration of an analyte (e.g., hydronium ions, potassium, glucose), or to provide some other function. The first and second electrodes 350 could be formed of a metallic and/or conductive material (e.g., polysilicon, aluminum, gold) during the formation of the integrated circuit 310. Additionally or alternatively, a layer of silver, silver chloride, platinum, gold, or some other material could subsequently be formed (e.g., by sputtering, by electroplating) on the surface of the electrodes 350.

In some examples, the electrodes 350 could be configured and/or operated to detect an analyte in interstitial (or other fluid) within skin or some other tissue within which the microelectronic device 300 is disposed. The electrodes 350 could detect the analyte electrochemically, e.g., by detecting a voltage between and/or a current passing through the electrodes 330 that is related to the concentration, presence, or some other property of the analyte. Thus, one of the electrodes 350 could be configured to act as a working electrode, with an immobilized analyte-sensitive substance 355 (e.g., a reagent, a protein, an enzyme) that selectively interacts with the analyte on or near the working electrode. Such an analyte-selective substance can be immobilized on the surface of the working electrode by crosslinking the substance into a crosslinked layer on the surface of the electrode. This could include using an aldehyde, dialdehyde (e.g., glutaraldehyde), or other crosslinking agents to form the crosslinked layer of the substance on the electrode surface. Additionally or alternatively, such an analyte-selective substance can be localized within an analyte-permeable polymer layer that is disposed on the working electrode.

The protective layer 340 is provided to protect the integrated circuit 310 from a tissue environment (e.g., from damage caused by a foreign body response), to protect tissues from the integrated circuit 310 (e.g., to prevent cytotoxic chemicals and/or surfaces of the integrated circuit 310 from damaging the tissue and/or emitting harmful chemicals into a body), to reduce and/or control a foreign body response of a body to the presence of the microelectronic device 200, or to provide some other functionality. As shown, the protective layer 340 includes windows 345 formed through the protective layer 340 to allow fluids and/or tissues in the environment of the microelectronic device 300 to contact the electrodes 350 and/or the analyte-sensitive substance 355. The protective layer 340 could include further windows or other features, e.g., to provide access to further sensors (e.g., electrodes, pressure sensors, analyte or fluid sensors), to provide means for mounting the integrated circuit 310 (e.g., attaching a suture or other connecting means to holes, tabs, or other formed features of the protective layer 340), or according to some other application.

The integrated circuit 310 further includes electronics (not shown) configured to operate the elements of the microelectronic device 300 to receive wireless power from an external source (e.g., to receive optical, radio frequency, or some other form of energy from an external reader device or some other power source), to detect physical variables and/or determine hemodynamic or physiological parameters of a body within which the microelectronic device 300 is disposed, to provide wireless transmissions of detected properties or parameters, and to provide other functions of the microelectronic device 300. Such a controller could include analog elements (e.g., amplifiers, filters, buffers, power conditioning circuits, analog oscillators), digital elements (e.g., analog-to-digital converters, microprocessors, comparators, logic gates, digital oscillators, memories), or other components configured to provide functions of the microelectronic device 300.

Note that the illustrated microelectronic device 300 is intended as a non-limiting example. Microelectronic devices as described herein could include more or fewer of the illustrated elements or could include additional elements (e.g., additional types of sensors, additional means for providing wireless indications). For example, a microelectronic device could wholly or partially enclose a portion of subsurface vasculature, e.g., could include a strain-sensitive extension configure to at least partially enclose a portion of subsurface vasculature such that expansion of the portion of subsurface vasculature (e.g., related to a pressure in the portion of subsurface vasculature, related to a volume of blood in the portion of subsurface vasculature) could deform the strain-sensitive extension, allowing the microelectronic device to detect a strain that is related to hemodynamic properties of the portion of subsurface vasculature.

Moreover, it is particularly noted that while sensors and implantable microelectronic devices including such sensors are described herein by way of example as a devices configured to be implanted beneath a skin surface of a person (e.g., proximate a portion of subsurface vasculature), it is noted that the disclosed microelectronic devices can be applied in other contexts as well. For example, microelectronic devices disclosed herein may be included in implantable devices used to measure a hemodynamic or physiological parameter or other information relating to an animal. In another example, microelectronic devices disclosed herein may be included in devices to measure a light intensity or other properties of a natural environment, a material or fluid that is part of an artificial process, such as a waste treatment process, pharmaceutical synthesis process, food preparation process, fermentation process, or medical treatment process, or to measure a light intensity or other properties of some other material or environment. Further, reader devices as described herein (i.e., reader devices including arrays of antenna coils configured to interact with such microelectronic devices) could be configured to be mounted to surfaces of and/or within such alternative environments.

V. Example Electronics of a Reader Device

Figure 4:
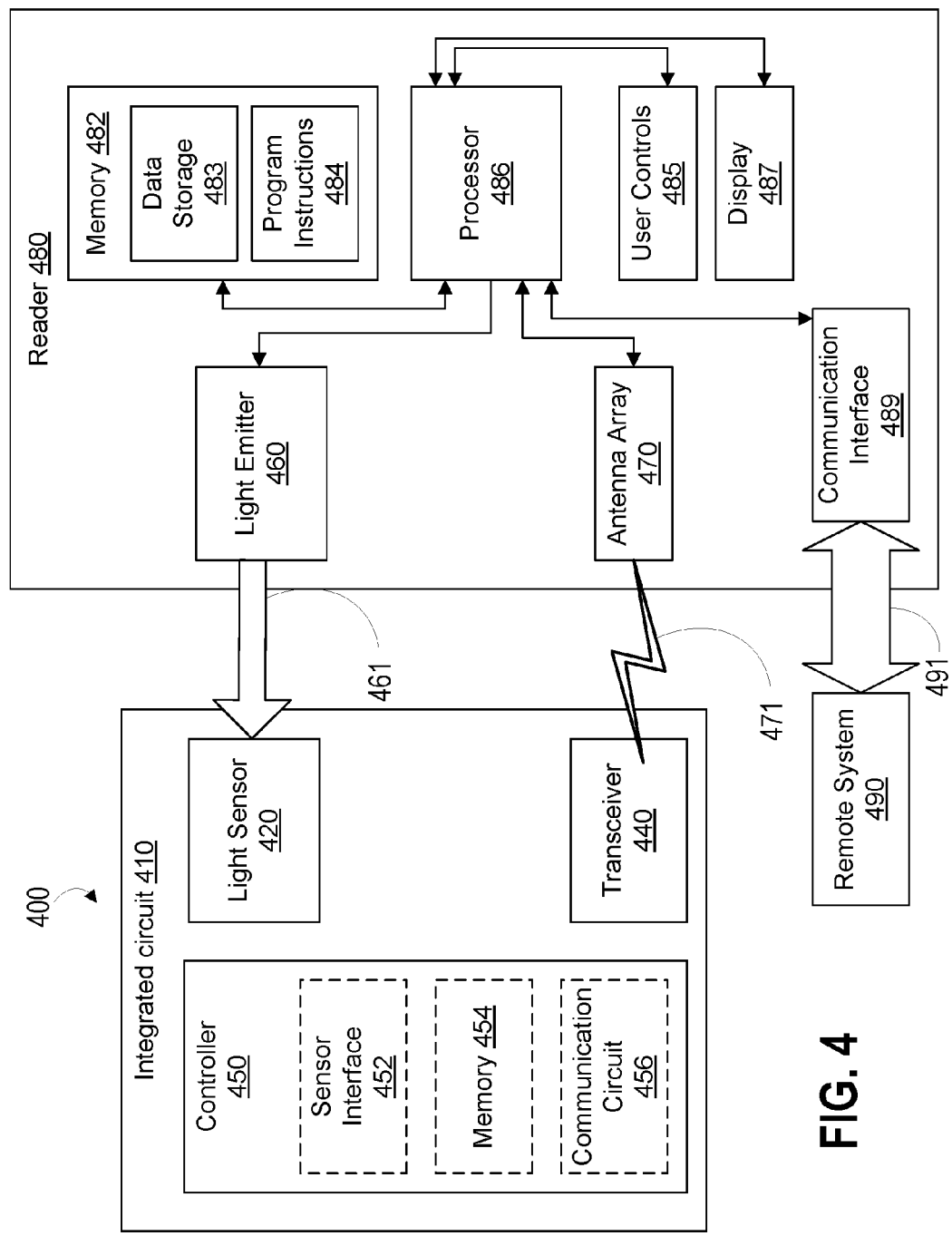
FIG. 4 is a block diagram of an example system that includes a microelectronic device in wireless communication with an external reader.

FIG. 4 is a block diagram of a system that includes an implanted microelectronic device 400 in wireless communication with an external reader device 480. The microelectronic device 400 includes a single integrated circuit 410 that provides one or more elements of the microelectronic device 400 (e.g., electronics, sensors, transmitters, energy receivers) and that is configured to be implanted or otherwise placed beneath a skin surface, e.g., such that a portion of subsurface vasculature is located between the microelectronic device 400 and the skin surface. As illustrated, the integrated circuit 410 provides a light sensor 420, a transceiver 440, and a controller 450. The transceiver 440 supplies operating voltages to the controller 450 and/or other elements of the microelectronic device 400 by receiving wireless power 471 from the external reader 480 and/or transmits wireless transmissions 471 to the external reader 480, via an antenna array 470. The light sensor 420 is configured to detect a property (e.g., an intensity) of light received from the environment of the microelectronic device 400, e.g., light that has been reflected by, scattered by, partially absorbed by, or otherwise transmitted through a portion of subsurface vasculature. Such light can be provided as illumination 461 provided by a light emitter 460 of the external reader 480, or can be provided from ambient light sources or some other source of illumination. The transceiver 440 can be operated by the controller 450 to provide wireless indications (e.g., radio frequency indications 471) related to information detected or determined using the light sensor 420 and/or related to some other information.

As shown, the transceiver 440, the controller 450, and the light sensor 420 are provided by the integrated circuit 410. However, one or more of these components, or elements thereof, could be attached to and/or formed on the integrated circuit 410 and/or provided in one or more further integrated circuits (e.g., one or more further integrated circuits soldered to, adhered to with an adhesive, or otherwise bonded to and electrically connected with the integrated circuit 410). For example, a coil or other antenna of the transceiver 440 could be provided as a loop of wire or other conductive elements formed on or otherwise disposed on the integrated circuit 410. In some examples, such elements, or further integrated circuits, could be connected to the integrated circuit 410 via one or more pads formed on the surface of the integrated circuit 410. Further, the integrated circuit 410 could be coated in a protective layer (e.g., a layer of polymer) or some other material covering to protect the integrated circuit 410, to control the interface between the microelectronic device 400 and surrounding tissues or fluids, to sensitize a sensor (e.g., an electrode) of the integrated circuit to an analyte of interest, to control a property of light received from the environment by the light sensor 420 (e.g., by forming and/or disposing an optical filter on the integrated circuit 410 over the light sensor 420).

The controller 450 formed in the integrated circuit 410 could include a variety of elements. For example, the controller 450 could include logic gates, arithmetic logic units, microprocessors, registers, digital oscillators, counters, logical buses, amplifiers, analog-to-digital converters (ADCs), mixers, analog oscillators, buffers, or some other component or components. Such components can be electrically connected via interconnects or traces formed (e.g., patterned) on or within the integrated circuit 410. The controller 450 can include analog components (e.g., amplifiers, buffers, current sources), logic elements (e.g., comparators, counters, digital clocks or oscillators), or other components (e.g., ADCs) configured to operate the light sensor 420 to detect the intensity or some other property of a received light, an encoder, mixer, amplifier, or other elements configured to provide wireless indications (e.g., light intensity levels, digital codes generated by an ADC, determined physiological or hemodynamic parameters) via the transceiver 440, and/or to provide other functions.

The transceiver 440 can be configured to receive radio frequency power from one or more antennas of the antenna array 470 to power the microelectronic device 400. In such examples, the transceiver 440 could include a loop antenna (e.g., a loop antenna formed from one or more layers and/or loops of conductive material formed one or within the integrated circuit 410 and/or formed from one or more loops of wire or other conductive material formed and/or disposed on the integrated circuit 410) that is configured to receive RF power from the external reader 480. In some examples, such an RF-power-receiving antenna can also be used to communicate with external devices by, e.g., transmitting a wireless transmission. The controller 450 or some other component of the implantable device 400 could include a rectifier or other components configured to generate, using the radio frequency power received via the transceiver 440, a voltage to power the implanted device 400. The controller 450 (or some other element of the implanted device 400) could include and ADC or other element(s) that are operable to measure the power received by the device 400 (e.g., by measuring a voltage across a rectifier that is coupled to an antenna coil of the transceiver 440) and such a measured power could be indicated wirelessly to the reader device 480 (e.g., to inform the operation of the antenna array 470 to provide radio frequency power to the implanted device 400).

The sensor interface module 452 could take a variety of forms according to the methods used to detect properties of light received by the light sensor 420 and/or the configuration or operation of further sensors of the microelectronic device 400 (not shown) used to detect other physical variables related to physiological and/or hemodynamic parameters of interest. The light sensor 420 could include a photodiode, a phototransistor, a photoresistive element, or some other components configured to output a voltage, a current, or some other electrical signal related to the intensity of a received light, the intensity of a received light within a specified range of wavelengths, the intensity of received light within a specified range of polarizations, the intensity of light received from a specified range of incident angles relative to the microelectronic device 400, or to detect some other properties of received light. The sensor interface module 452 could include amplifiers, transimpedance amplifiers, filters, buffers, voltage references, ADCs, or other components configured to operate the light sensor 420 (or some other sensor(s)) to output a signal (e.g., to generate one or more digital codes) related to the detected property of light received by the light sensor 420.

Additional or alternative sensors can be operated by the sensor interface module 452. Such sensors could include temperature sensors, strain sensors, accelerometers, gyroscopes, pressure sensors, electric or magnetic field sensors, electrodes or other elements configured to detect a potential and/or current between two or more locations of tissue or fluid that are in contact with the electrodes, analyte sensors, or some other types of sensors.

The sensor interface 452 can include an ADC configured to receive an electrical signal that is generated by the light sensor 420 (or some other sensor of the microelectronic device 400) and/or elements of the sensor interface 452 that are related to a hemodynamic and/or physiological parameter, e.g., to a blood flow rate, a blood oxygenation, a volume of blood in skin, or some other physical variable, and generate a digital code. The electrical signal could be a signal generated by an electrode, an amplifier, a buffer, a photodetector, a multiplexer, or some other electronic component(s) of the microelectronic device 400. Further, the generated digital code could be related to a voltage, current, frequency, pulse rate, inter-pulse interval, or some other property of the electrical signal. The ADC could include a direct-conversion ADC, a successive approximation ADC, a ramp-compare ADC, a pipeline ADC, a sigma-delta ADC, or some other type of ADC and/or electronic components configured to generate digital codes based on properties of received electrical signals. Additionally or alternatively, a signal related to a property of interest could be used by analog electronics of the device 400 (e.g., to control a voltage-controlled oscillator to control a frequency, phase, or other property of a wireless transmission transmitted by the transceiver 440) to provide an indication related to a property of interest.

The memory 454 could include a variety of volatile and nonvolatile electronic storage elements configured to provide means for the microelectronic device 400 to record and/or log information (e.g., digital codes) related to a detected and/or determined physiological property (e.g., related to intensities of received light, related to a blood oxygen content), calibration information, and/or other information detected by or input to the microelectronic device 400. For example, the memory 454 could include one or more EEPROM memories, flash memories, NVRAM memories, DRAM memories, SRAM memories, flip-flops, or other information storage elements. The memory 454 could have an information storage capacity sufficient to record some specified period of information detected using the light sensor 420 (e.g., digital codes generated based on a signal generated by the light sensor 420) at some specified rate of detection. Additionally or alternatively, the microelectronic device 400 could be in communication with a memory that is external to the microelectronic device 400 and that could be used as described above (e.g., to store generated digital codes, to store and/or access calibration or other configuration data of the microelectronic device 400).

The controller 450 includes a communication circuit 456 for providing wireless transmissions to one or more antenna coils of the antenna array 470 via the transceiver 440 or to the reader device 480 via some other indicating means (e.g., via an LED, a VCSEL, a laser, or some other light-emitting means of the implanted device 400 emitting optical signals to a photodiode or other light-detecting means of the reader device 480). The communication circuit 456 can optionally include one or more oscillators, mixers, frequency injectors, etc. to modulate and/or demodulate information on a carrier frequency to be transmitted as a radio frequency indication by a coil, antenna, or other elements of the transceiver 440. In some examples, the microelectronic device 400 is configured to transmit information (e.g., generated digital codes, values of a physiological parameter determined therefrom) by modulating an impedance of an antenna (e.g., a loop antenna or coil) of the transceiver 440 in a manner that is perceivable by one or more antenna coils of the antenna array 470 of the external reader 480. For example, the communication circuit 456 can cause variations in the amplitude, phase, and/or frequency of backscatter radiation from the antenna of the transceiver 440, and such variations can be detected by one or more antenna coils of the antenna array 470. Such wireless communication could be compatible with one or more existing backscatter wireless communications standards, e.g., RFID. Additionally or alternatively, the communication circuit 456 and transceiver 440 could be configured to transmit wireless signals according to some other method, e.g., according to the Bluetooth (e.g., Bluetooth Low Energy), ZigBee, WiFi, LTE, and/or some other wireless communications standard or scheme. In some examples, such communications (e.g., data transmitted from the microelectronic device 400) could be cryptographically secured; that is, the wireless communications link could be encrypted.

It is noted that the block diagram shown in FIG. 4 is described in connection with functional modules for convenience in description. However, embodiments of the microelectronic device 400 can be arranged with one or more of the functional modules ("sub-systems") implemented in a single integrated circuit (e.g., 410), multiple integrated circuits physically and electrically bonded together, one or more loops of wire or other elements formed and/or disposed on such an integrated circuit(s), or according to some other consideration.

The external reader 480 includes an antenna array 470. The antenna array includes a plurality of antenna coils that span a specified area (e.g., of a skin surface beneath which the microelectronic device 400 is disposed) and that have respective degrees of electromagnetic coupling with an antenna of the transceiver 440. The antenna array 470 is operable to select one or more antenna coils of the array 470 (e.g., using a radio frequency switch) and to operate the selected antenna coil(s) to provide radio frequency power 471 to the microelectronic device 400 via an antenna of the transceiver 440. In some examples, the one or more antennas used to provide radio frequency power to the microelectronic device 400 could additionally be used to detect an amount of the transmitted radio frequency power that is backscattered or otherwise reflected by the microelectronic device 400 to provide a wireless transmission of information to the reader device 480. The antenna array 470 and/or antenna coils thereof could be configured to perform further functions, e.g., to transmit wireless transmissions to the microelectronic device 400, to detect the location, orientation, or depth of the microelectronic device 400, or some other functions.

The external reader 480 further includes a light emitter 460. The light emitter 460 is configured to provide illumination 461 that can be received by the light sensor 420 of the microelectronic device 400. The light emitter 460 could include one or more LEDs, lasers, or other light-emitting elements configured to emit light having a specified wavelength, spectral content, degree or direction of polarization, coherence length, or some other property specified according to an application. Such illumination could be scattered by, partially absorbed by, fluorescently absorbed and re-emitted, reflected by, or otherwise transmitted through a portion of subsurface vasculature or other tissue or target of interest. A property of such interaction between the emitted light and the target of interest (e.g., blood in a portion of subsurface vasculature) could be detected by the light sensor 420, e.g., to determine one or more properties of the target. For example, an amount of absorption of light by blood in a portion of subsurface vasculature at one or more wavelengths could be related to a volume of blood in the portion of subsurface vasculature, an oxygen content of the blood, or some other properties. Additionally or alternatively, a time-varying pattern of constructive and destructive interference in coherent light scattered by or otherwise transmitted through blood in a portion of subsurface vasculature could be related to the velocity (e.g., a distribution of velocities) of blood cells flowing in the portion of subsurface vasculature. The light emitter 460 could emit light continuously, in pulses, or according to some other pattern. Further, the light emitter 460 could be operated to optically indicate information, e.g., in a coded pattern of light pulses, that could be detected by the controller 450 using the light sensor 420.

The memory 482 can also include program instructions 484 for execution by the processor 486 to cause the external reader 480 to perform processes specified by the instructions 484. For example, the program instructions 484 can cause external reader 480 to perform any of the functions described herein. For example, program instructions 484 may cause the external reader 480 to provide a user interface that allows for retrieving information communicated from the microelectronic device 400 (e.g., digital codes generated by the sensor interface 452, values of a physiological parameter determined therefrom by the controller 450) by displaying that information on the display 487 in response to commands input through the user controls 485. The external reader 480 can also include one or more hardware components for operating the antenna array to select one or more antenna coils of the antenna array 470, to receive radio frequency signals 471 from the microelectronic device 400 using the selected antenna coils, to provide radio frequency power 471 to at least partially power the microelectronic device 400 using the selected antenna coils, or to perform some other functions (e.g., to transmit a wireless transmission to the microelectronic device 400). The external reader 480 can also include one or more hardware components for operating the light emitter 460 to illuminate 461 a target of interest (e.g., a portion of subsurface vasculature), or to perform some other operations.

The external reader 480 can also be configured to include a communication interface 489 to communicate signals via a communication medium 491 to and from a remote system 490. For example, the remote system 490 may be a smart phone, tablet computer, laptop computer, or personal computer, and communication interface 489 and communication medium 491 may be a Bluetooth module and wireless Bluetooth communication signals, respectively. In this example, the external reader 480 may be configured to send information about the physiological parameter or other information detected or determined by the microelectronic device 400 to the smart phone, tablet computer, laptop computer, or personal computer for storage and offline analysis. In another example, the remote system 490 is a server at a clinic or physician's office, the communication interface 489 is a WiFi radio module, and the communication medium 491 is a network sufficient to enable the transfer of data between the remote server and the WiFi radio module. A physician may use this data to make determinations or diagnoses related to the subject's condition. Further, the external reader 480 may be configured to receive signals from a remote server, such as instructions sent by a physician at a remote location to, for example, increase or decrease sampling frequency. Communication interface 389 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 480 can be a smart phone, digital assistant, or other portable computing device with wireless connectivity sufficient to provide the wireless communication link 471 and/or wireless power 471. The external reader 480 can also be implemented as an antenna array module that can be plugged in to a portable computing device, such as in an example where the wireless communication link 471 and/or wireless power 471 include electromagnetic fields and/or waves at carrier frequencies not commonly employed in portable computing devices. In some instances, the external reader 480 is a special-purpose device configured to be periodically placed relatively near the microelectronic device 400 to allow the wireless communication link 471 and/or wireless power link 471 to operate with a low power budget.

As described elsewhere herein, one or more particular antenna coil(s) of an array of such antenna coils (e.g., 140, 470) can be selected and operated to provide radio frequency power to an implanted device or to perform some other operations (e.g., to receive wireless signals from such an implanted device). Such an antenna array and/or antenna coils thereof can be configured in a variety of ways to provide this functionality. In some examples, each of the antenna coils could be coupled to a respective receiver and/or transmitter, and selection of a particular antenna coil could include selecting and operating the receiver and/or transmitter of the selected antenna coil while disabling or otherwise operating receivers and/or transmitters of non-selected antenna coils. For example, receivers and/or transmitters of non-selected antenna coils could be operated to connect the non-selected antenna coils to respective specified high impedances (e.g., to electrically disconnect the non-selected antenna coils from other components) or specified low impedances (e.g., to electrically short the terminals of the non-selected antenna coils) to, e.g., prevent the non-selected antenna coils from interfering with the operation of the selected antenna coil to provide wireless power, to receive wireless transmissions, or to perform some other functions.

Additionally or alternatively, all of the antenna coils of an antenna array (or a subset of the antenna coils of an antenna array) could be coupled, via a radio frequency (RF) switch, to one or more receivers and/or transmitters. In such an example, operating a selected antenna coil could include operating the RF switch to couple the selected antenna coil to a respective receiver and/or transmitter. In such an example, each antenna coil could be coupled to the RF switch via a respective modulator that is operable to control an amplitude and phase of the radio frequency power emitted from the antenna coil relative to the radio frequency power emitted from other selected antenna coil(s). Such a modulator could include an attenuator, a phase shifter, one or more impedance matching circuits, or other elements configured to control an amplitude and/or relative phase of radio frequency power emitted from a respective antenna coil (e.g., by attenuating and/or phase shifting radio frequency power received from an RF switch) and/or to match an impedance of a respective antenna to the output of an RF switch or other components coupled to the modulator and/or antenna coil.

Figure 5:
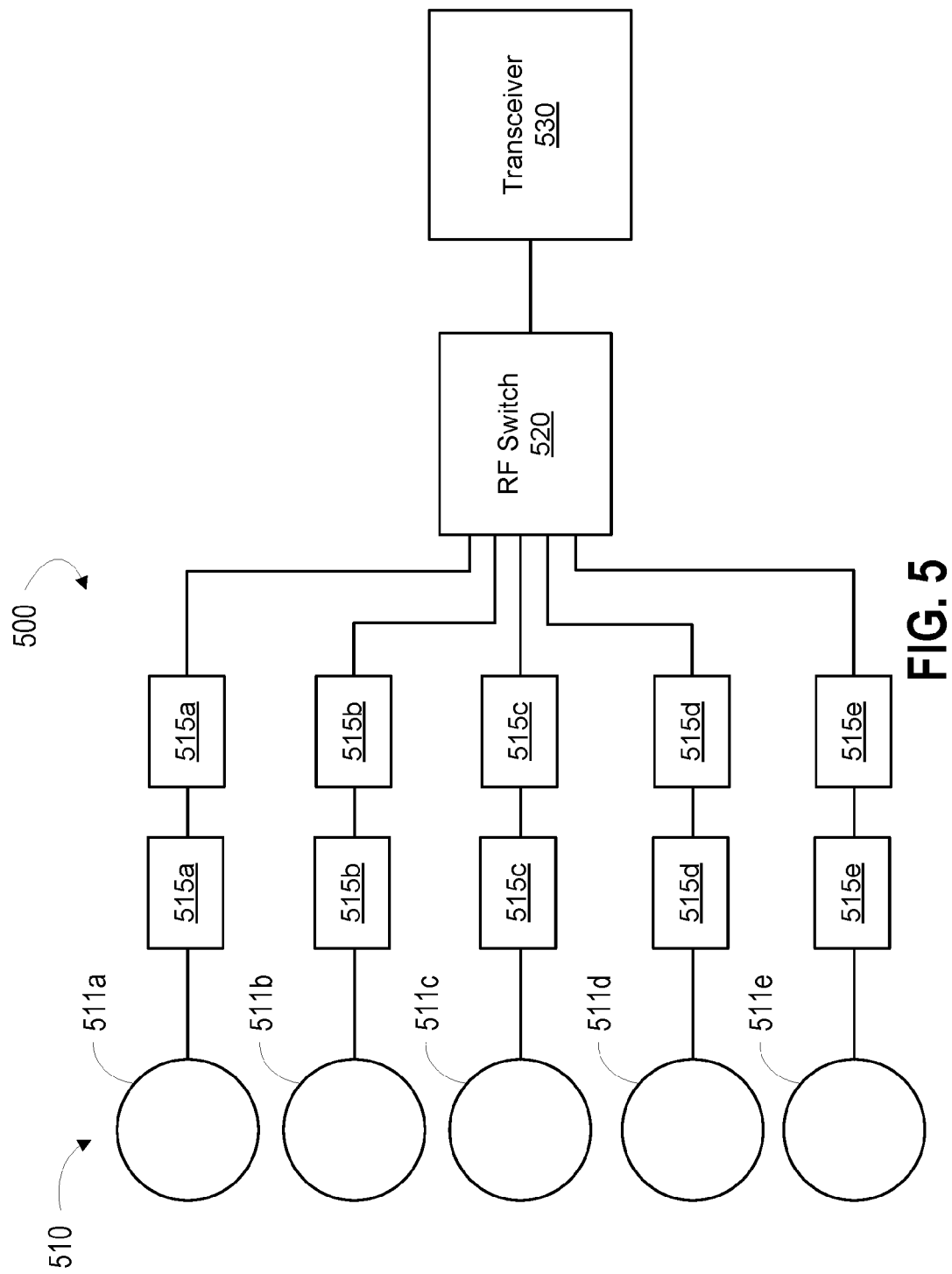
FIG. 5 is a block diagram of an example system that includes an antenna array that can be operated to communicate with a microelectronic device.

To illustrate this, FIG. 5 shows elements of a reader device 500. The elements include antenna coils 551a-e of an array of antenna coils 510 (that is, e.g., configured to span a specified area of skin surface when the array is mounted to such a skin surface) that are electrically connected, via respective modulators 515a-e and matching circuits 525a-e, to an RF switch 520. The RF switch is, in turn, connected to a transceiver 530.

The RF switch 520 could include a variety of components configured to selectably couple one of the antenna coils 511a-e (via a respective modulator 515a-e and matching circuit 525a-e) to the transceiver 530. The RF switch 520 could include one or more transistors, field effect transistors, bipolar transistors, junction field effect transistors, relays, or other electrical switching elements that are controllable to selectably couple one or more terminals of a selected antenna coil (via a corresponding modulator and matching circuit) to the transceiver 530. Further, the RF switch 520 could be configured and/or operated to couple non-selected antenna coils to respective specified high or low impedances, e.g., to reduce interference to the operation of the selected antenna coil (e.g., to provide wireless power, to receive wireless transmissions) by the non-selected antenna coils.

The modulators 515a-e can each include a variety of components configured to control an amplitude and/or a relative phase of radio frequency power transmitted through the modulator (e.g., from the RF switch 520 to a respective antenna coil 511a-e) and/or to match an impedance of components coupled to the modulator. The modulators 515a-e can each include amplifiers, RF switches, transistors, fixed delay lines, varactors, MEMs devices, transformers, or other components configured as phase shifters, impedance matching elements, attenuators, amplifiers, or other elements to provide functionality of a modulator as described herein. Such components could be formed on one or more monolithic microwave integrated circuits. One or more analog signals (e.g., voltages, currents) could be applied to control an amount of attenuation, amplification, and/or phase shifting applied by a modulator 515a-e (e.g., by applying a voltage to control an RF capacitance of a varactors, by applying a current to control an RF impedance of a PIN diode). Additionally or alternatively, one or more digital signals could be applied to control an amount of attenuation, amplification, and/or phase shifting applied by a modulator 515a-e (e.g., by applying a voltage to control one or more RF switches to control whether a delay line or other component is part of an RF signal path through the modulator).

The transceiver 530 could include a variety of amplifiers, buffers, oscillators, filters, modulators, or other elements configured to provide wireless power, via one or more selected antenna coils 511a-e, to an implanted device. The transceiver 530 could additionally be configured to receive a wireless transmission, via one or more selected antenna coils 511a-e, from the implanted device. The transceiver 530 could be configured to perform both operations, or to additionally perform further operations, e.g., to transmit wireless transmissions, via one or more selected antenna coils 511a-e, to an implanted device. In some examples, the transceiver 530 could be configured to provide radio frequency power, via one or more selected antenna coils, to an implanted device and to receive a radio frequency transmission, via the selected one or more antenna coils, as an amount of the provided wireless power that is backscattered or otherwise reflected by an antenna of the implanted device.

In some examples, an impedance of ports of different components of the reader device 500 could be substantially different, e.g., antenna coils 511a-e, the transceiver 530, and/or the RF switch 520 could have electrically coupled ports that are substantially different. In such examples, matching circuits (e.g., 525a-e) can be provided to match the impedance between components of the reader device 500. Such matching circuits could include coils, chokes, capacitors, striplines, stubs, resistors, or other components configured to transfer radio frequency energy or signals between components of the reader device 500. Such matching circuits could have additional functions, e.g., the matching circuits 525a-e provided between the modulators 515a-e and respective antenna coils 511a-e could set a resonance frequency, a quality factor, or some other properties of the antenna coils 511a-e.

In some examples, such matching circuits (e.g., 525a-e) could be controllable (e.g., could include one or more switches, controllable resistances, controllable impedances, or other electrical elements having controllable electrical properties) and could be controlled according to the identity of the antenna coils of a selected set of operated antenna coils, according to the location of such selected antenna coils within the array of antenna coils 510, according to electrical properties of the array 510 (e.g., according to the electrical properties of skin proximate the array 510), to compensate for differences (e.g., lengths, widths) between the feedlines used to transfer signals between each of the antenna coils 510a-e and the RF switch 520, or according to some other consideration. Alternatively, one or more of such matching circuits could be static, that is, could have electrical properties (e.g., input impedance, output impedance, amplitude and/or phase transfer function) that are not controllable. Such electrical properties could be specified, e.g., to compensate for differences between the feedlines used to transfer signals between each of the antenna coils 510a-e and the RF switch 520 or according to some other consideration.

Note that, in some examples, impedance-matching elements of the modulators 515a-e and/or the matching circuits 525a-e could be omitted, e.g., because an impedance of a port of the RF switch 520 substantially matches an impedance of the antenna coils 511a-e. Additionally or alternatively, further matching circuits (e.g., between the RF switch 520 and the transceiver 530) could be provided to facilitate transfer of radio frequency signals between elements of the reader device 500.

The circuit 500 shown in FIG. 5 includes a number of modulators 515a-e configured to modify an amplitude and/or relative phase of radio frequency power that is emitted from a common transmitter and applied to a number of different antenna coils such that the different antenna coils can be operated to provide radio frequency power at respective different amplitudes and/or relative phases. Alternatively, two or more transmitters and/or receivers could be provided as a part of a circuit to provide radio frequency power at respective different amplitudes and/or relative phases, and the provided radio frequency power at respective different amplitudes and/or relative phases can be provided to respective different antenna coils such that the radio frequency power emitted from each of the antenna coils has a respective different amplitude and/or relative phase.

Figure 6:
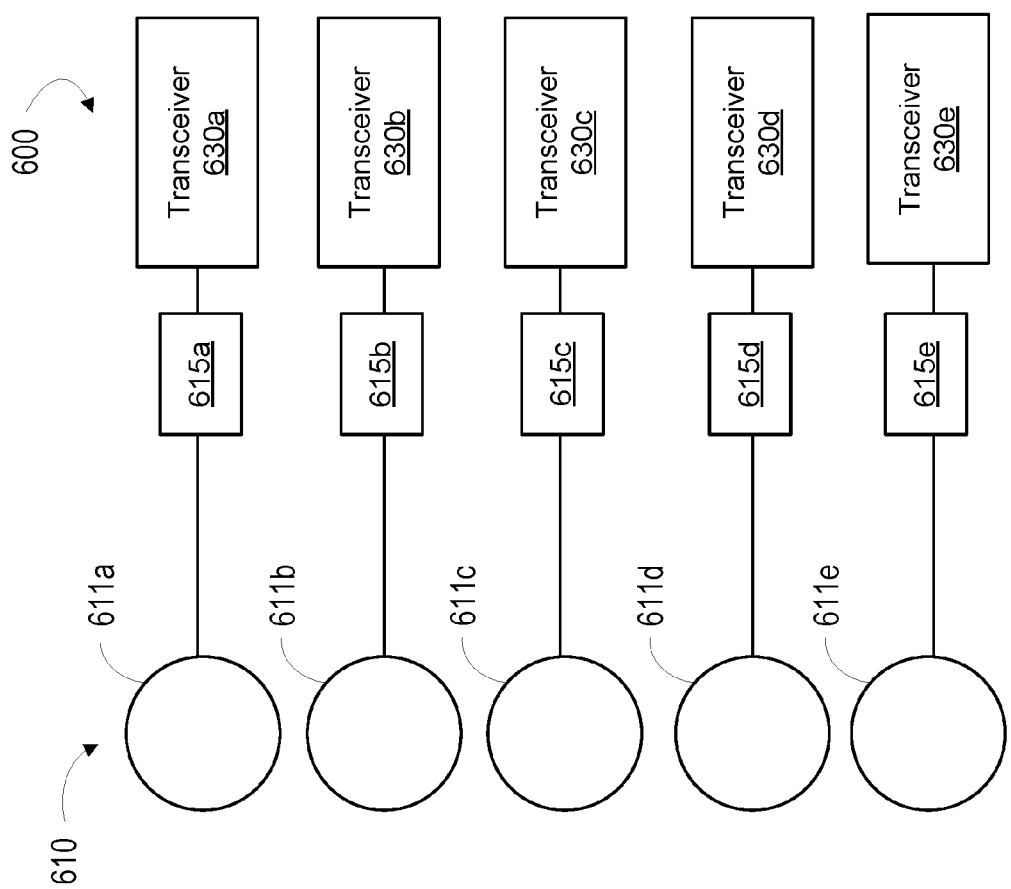
FIG. 6 is a block diagram of an example system that includes an antenna array that can be operated to communicate with a microelectronic device.

In a first example, each antenna coil could be coupled to a respective transmitter and/or receiver that is configured to provide radio power at a respective amplitude and/or relative power, or to provide no radio frequency power (e.g., when a corresponding antenna coil is not selected as described elsewhere herein). FIG. 6 shows elements of a reader device 600 that is configured in this way. The elements include antenna coils 651a-e of an array of antenna coils 610 (that is, e.g., configured to span a specified area of skin surface when the array is mounted to such a skin surface) that are electrically connected, via respective matching circuits 615a-e, to respective transceivers 630a-e.

Each transceiver 630a-e could include a variety of amplifiers, buffers, oscillators, filters, modulators, or other elements configured to provide radio frequency power, via a respective antenna coil 611a-e, to an implanted device. Each transceiver 630a-e could additionally be configured to receive a radio frequency signal, via a respective antenna coil 611a-e, from an implanted device. Each transceiver 630a-e could be configured to perform both operations, or to additionally perform further operations, e.g., to transmit wireless transmissions, via respective antenna coils 611a-e, to an implanted device.

In some examples, an impedance of the transceivers 630a-e could be substantially different from the antenna coils 611a-e to which the transceivers 630a-e are electrically coupled. In such examples, matching circuits 615a-e can be provided to match the impedance between components of the reader device 600. Such matching circuits could include coils, chokes, capacitors, striplines, stubs, resistors, or other components configured to transfer radio frequency energy or signals between components of the reader device 600. Such matching circuits could have additional functions, e.g., the matching circuits 615a-e provided between the transceivers 630a-e and the antenna coils 611a-e could set a resonance frequency, a quality factor, or some other properties of the antenna coils 611a-e. Note that, in some examples, the antenna coil matching circuits 615a-e could be omitted, e.g., because an impedance of the transceivers 630a-e substantially matches an impedance of the antenna coils 611a-e.

Figure 7:
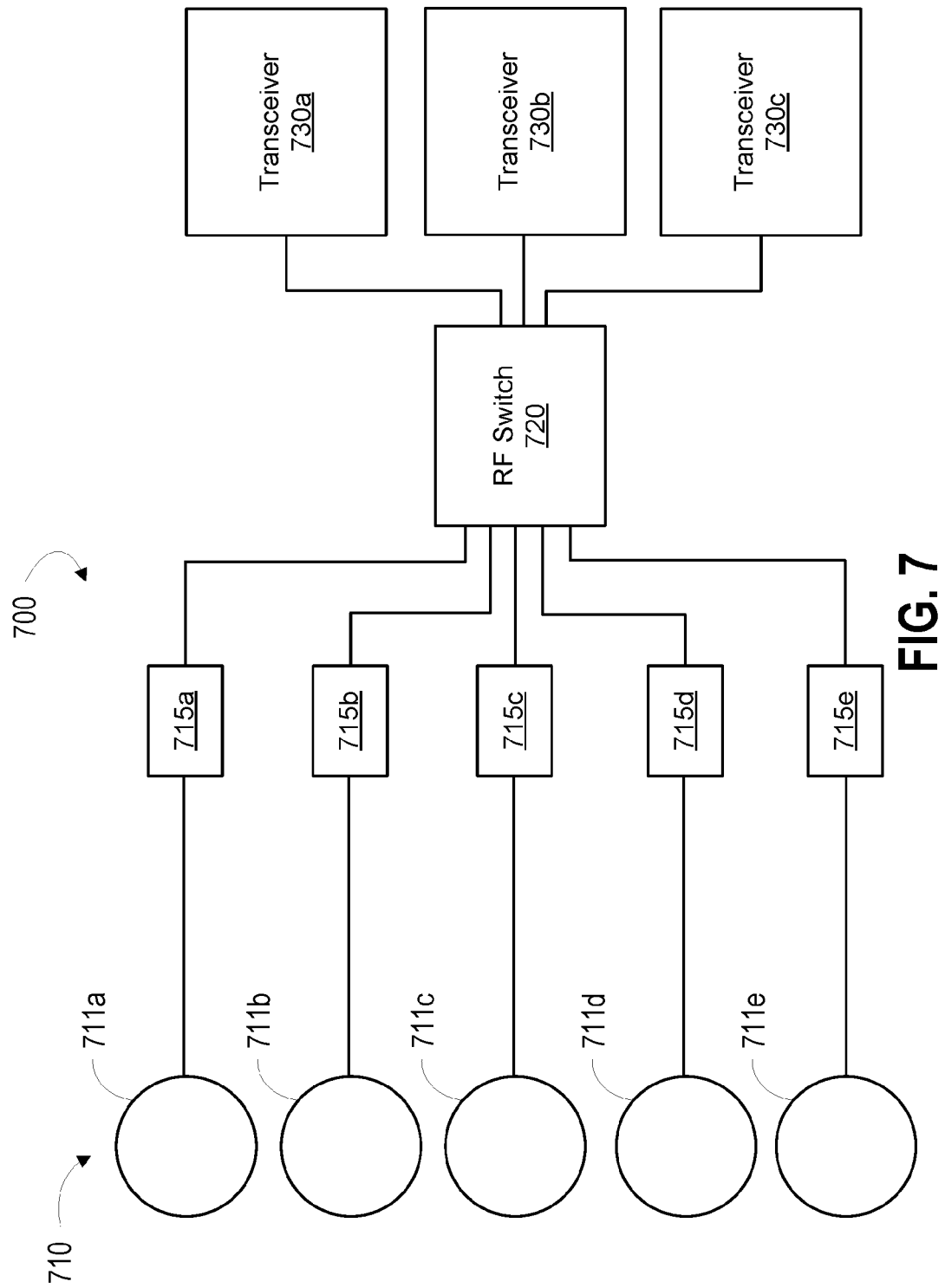
FIG. 7 is a block diagram of an example system that includes an antenna array that can be operated to communicate with a microelectronic device.

In another example, each antenna coil of a set of selected antenna coils could be coupled, via an RF switch, to a respective transmitter and/or receiver that is configured to provide radio power at a respective amplitude and/or relative power. FIG. 7 shows elements of a reader device 700 that is configured in this way. The elements include antenna coils 751a-e of an array of antenna coils 710 (that is, e.g., configured to span a specified area of skin surface when the array is mounted to such a skin surface) that are electrically connected, via respective matching circuits 715a-e, to an RF switch 720. The RF switch is, in turn, connected to transceivers 730a-c.

The RF switch 720 could include a variety of components configured to selectably couple each antenna coil of a selected set of one or more of the antenna coils 711a-e (via a respective matching circuit 715a-e) to a respective transceiver 730a-c. The RF switch 720 could include one or more transistors, field effect transistors, bipolar transistors, junction field effect transistors, relays, or other electrical switching elements that are controllable to selectably couple one or more terminals of a selected antenna coil (via a corresponding matching circuit) to a respective transceiver 730a-c). Further, the RF switch 720 could be configured and/or operated to couple non-selected antenna coils to respective specified high or low impedances, e.g., to reduce interference to the operation of the selected antenna coil (e.g., to provide wireless power, to receive wireless transmissions) by the non-selected antenna coils.

Each transceiver 730a-c could include a variety of amplifiers, buffers, oscillators, filters, modulators, or other elements configured to provide radio frequency power, via a respective selected antenna coil (e.g., one or more of 711a-e), to an implanted device. Each transceiver 730a-c could additionally be configured to receive a radio frequency signal, via a respective selected antenna coil, from an implanted device. Each transceiver 730a-c could be configured to perform both operations, or to additionally perform further operations, e.g., to transmit wireless transmissions, via respective selected antenna coils, to an implanted device.

In some examples, an impedance of ports of the RF switch 720 could be substantially different from components, e.g., antenna coils 711a-e, transceivers 730a-c, to which the RF switch 720 is electrically coupled. In such examples, matching circuits (e.g., 715a-e) can be provided to match the impedance between components of the reader device 700. Such matching circuits could include coils, chokes, capacitors, striplines, stubs, resistors, or other components configured to transfer radio frequency energy or signals between components of the reader device 700. Such matching circuits could have additional functions, e.g., the matching circuits 715a-e provided between the RF switch 720 and the antenna coils 711a-e could set a resonance frequency, a quality factor, or some other properties of the antenna coils 711a-e.

Note that, in some examples, the antenna coil matching circuits 715a-e could be omitted, e.g., because an impedance of a port of the RF switch 720 substantially matches an impedance of the antenna coils 711a-e. Additionally or alternatively, further matching circuits could be provided to couple other components of the reader device 700, e.g., to match an impedance between a port of the RF switch 720 and a corresponding transceiver 730a-c.

Note that the illustrated components of the microelectronic device 400 and external readers 480, 500, 600, 700 are intended as a non-limiting example embodiments and that microelectronic devices and/or external readers as described herein may include more or fewer of the illustrated elements and/or may include further elements. For example, an external reader 480 may not include a light emitter (e.g., 460). In such examples, a target of interest (e.g., a portion of subsurface vasculature) may be illuminated by some other source of light (e.g., ambient light sources). Further examples of implanted devices and external readers configured to power, receive wireless transmissions from, or otherwise interact with such implanted devices are anticipated.

VI. Example Methods

Figure 8:
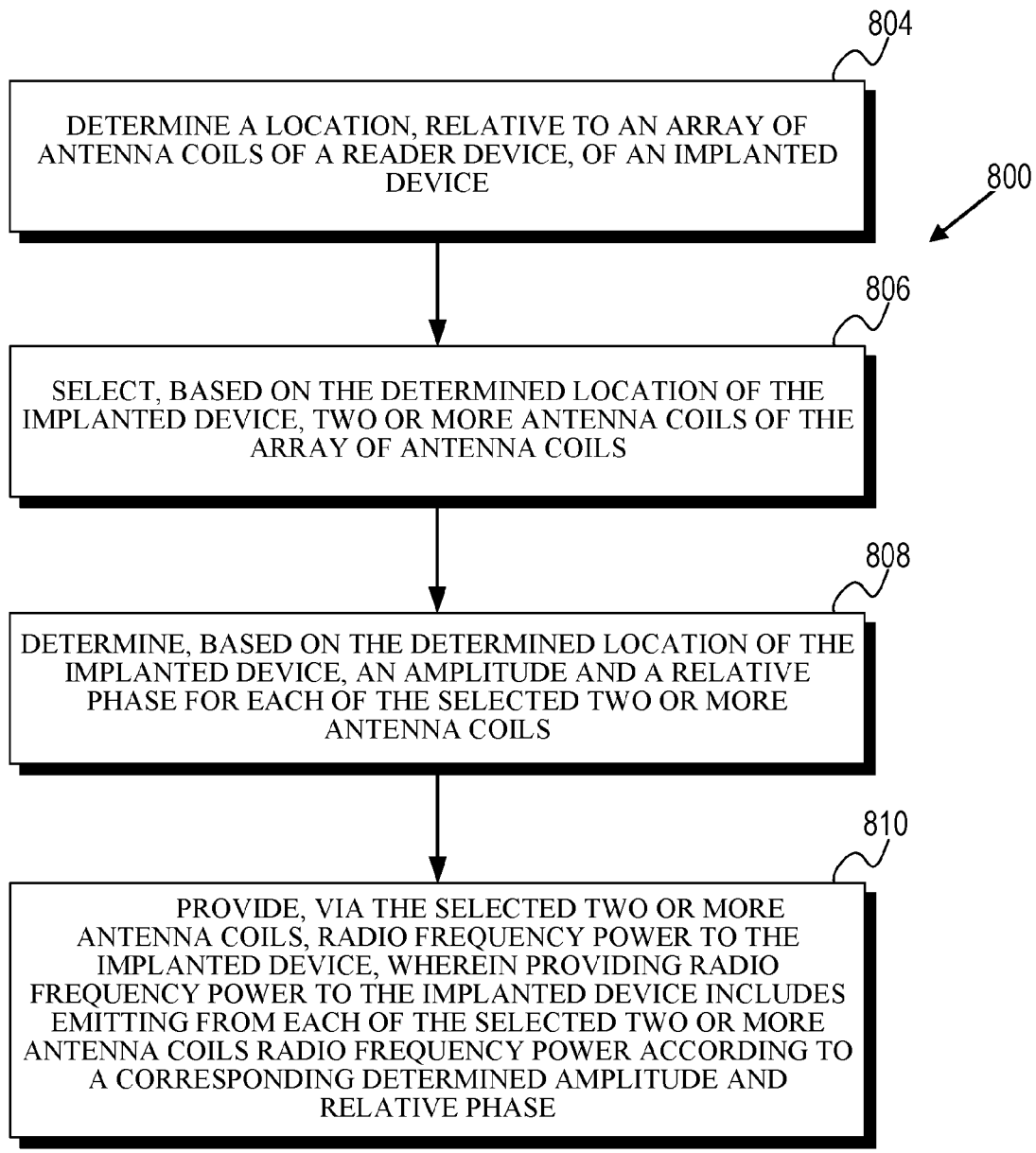
FIG. 8 is a flowchart of an example method for operating a reader device.

FIG. 8 is a flowchart of a method 800 for operating a reader device, e.g., a reader device as described elsewhere herein. The reader device is configured to operate in combination with (e.g., to provide energy to, to receive wireless transmissions from) a microelectronic or otherwise configured device that is implanted in tissue beneath a skin surface. The reader device includes an array of antenna coils the span a specified area of the skin surface. Each antenna coil of the array has a respective degree of electromagnetic coupling with an antenna of the implanted device.

The method 800 includes determining a location of an implanted device relative to the array of antenna coils (804). In some examples, the array of antenna coils could be operated to detect a degree of electromagnetic coupling between the implanted device and each of the antenna coils of the array. This could include providing, from each of the antenna coils in turn, radio frequency power to the implanted device. A signal strength of radio frequency signals scattered by, reflected from, or otherwise received from the implanted device by each antenna coil, in response to the antenna coil providing the radio frequency power (e.g., during a respective period of time), could be detected and used to determine the location and/or orientation of the implanted device. Additionally or alternatively, the implanted device could measure an amount of radio frequency power received from each of the antenna coils (e.g., during respective different periods of time) and could provide wireless transmissions indicative of the amount of radio frequency power received by the implanted device. This could include, e.g., measuring a magnitude of a voltage output from a radio frequency rectifier that is coupled to an antenna of the implanted device. Detected signal strengths, received wireless transmissions, or other information related to the location and/or orientation of the implanted device could be applied to a lookup table or used in some other way to determine a location and/or orientation of the implanted device relative to the array of antenna coils. Additionally or alternatively, the location and/or orientation of the implanted device relative to the array of antenna coils could be determined based on light reflected by, scattered by, or otherwise emitted from the implanted device and detect by light sensors (e.g., photodiodes, cameras) of the reader device.

The method 800 further includes selecting, based on the determined location of the implanted device, two or more antenna coils of the array of antenna coils (806) and determining, based on the determined location of the implanted device, an amplitude and a relative phase for each of the selected two or more antenna coils (808). This could include using a model of the electrical properties of the array of antenna coils, skin and other tissue, and the implanted device to determine the identity of antenna coils to select and the amplitude and relative phase of the radio frequency power emitted via the selected antenna coils using a method of optimization. Such a method of optimization could include a genetic algorithm, dynamic programming, gradient descent, or some other methods or combinations of methods. The method used could operate to increase an amount of power received by the implanted device, to increase the efficiency of the power transfer, or according to some other considerations as described herein. Such optimizations could be performed by a controller of a device that includes the array of antenna coils. Additionally or alternatively, such optimizations could be performed for a range of different locations and/or orientations of an implanted device relative to an array of antenna coils and the optimizations could be used to determine information for one or more lookup tables that could be used to determine, based on a location and/or orientation of an implanted device, a set of antenna coils to use to provide radio frequency power and, in examples wherein two or more antenna coils are selected, an amplitude and relative phase of radio frequency power to emit from each of the selected antenna coils.

The coils could be selected (806) and amplitudes and relative phases could be determined for each of the selected antenna coils (808) according to a variety of considerations, e.g., to increase an amount of power received by the implanted device, to reduce an amount of power absorbed by skin or other tissues, to reduce a maximum amount of power absorbed by a particular volume or area of skin or other tissues (e.g., to maintain the maximum volume or area density of radio frequency power absorbed by the skin), or according to some other considerations. This could include specifying the amplitudes and relative phases of the radio frequency power emitted from each of the selected antenna coils such that the near-field radio frequency fields generated by the antenna array exhibits a pattern of constructive and destructive interference within the skin. The amplitudes and relative phases could be specified such that the pattern of constructive and destructive interference satisfies some considerations, e.g., such that the location of an implanted device is within a region of constructive interference within the exhibited pattern of constructive and destructive interference and/or such that a direction of maximal radio frequency field intensity is aligned, at the location of the implanted device, with a characteristic direction of an antenna or other radio frequency power-receiving element(s) of the implanted device.

The method 800 further includes providing, via the selected two or more antenna coils, radio frequency power to the implanted device, wherein providing radio frequency power to the implanted device includes emitting from each of the selected two or more antenna coils radio frequency power according to a corresponding determined amplitude and relative phase (810). This could include operating a radio frequency switch to couple the selected antenna coils to one or more radio frequency transmitters. This (810) could additionally include operating such one or more radio frequency transmitters to generate radio frequency power, e.g., at one or more respective amplitudes and/or relative phases. Additionally or alternatively, providing, via the selected two or more antenna coils, radio frequency power to the implanted device (810) could include operating one or more modulators to attenuate, amplify, and/or phase shift radio frequency power that is generated by a transmitter and transmitting the attenuated, amplified, and/or phase-shifted radio frequency power via an antenna coil such that the radio frequency power emitted via the antenna coil has a specified amplitude and/or relative phase.

The method 800 could include additional steps. The method 800 could include transmitting light to the implanted device (e.g., through a portion of subsurface vasculature) such that a light sensor of the implanted device detects a portion of the transmitted light that has been scattered by, reflected by, partially absorbed by, or otherwise transmitted through a target of interest (e.g., the portion of subsurface vasculature). In such examples, a property (e.g., an intensity) of the received light that is detected by the light sensor of the implanted device could be related to a volume of blood in the portion of subsurface vasculature, an oxygen content of such blood, a pressure or flow rate of such blood, or some other hemodynamic or other properties of the target (e.g., a portion of subsurface vasculature and/or blood therein). The method 800 could include determining, by the reader device, such a hemodynamic or other property based on a wireless transmission received from the implanted device (using the selected antenna) that is related to the detected physical variable (e.g., an intensity of received light) detected using the light sensor or some other type of sensor of the implanted device at one or more points in time, e.g., determining a pulse rate, pulse timing, blood pressure, or other properties of a portion of subsurface vasculature and/or blood therein based on received indications of an intensity of light transmitted through the portion of subsurface vasculature and detected using the light sensor at a plurality of different points in time. Emitted light could additionally or alternatively be used to provide optical power to the implanted device, to provide optical wireless transmissions (e.g., commands, programming) to the implanted device, or to provide some other functions. A reader device could include an array of light emitters, and each antenna coil of the reader device could be associated with one or more of the light emitters. Light emitters of such an array could be operated (e.g., to provide illumination, as described above) based on the determined location of the implanted device, i.e., one or more light emitters associated with the location of the implanted device could be operated to provide the illumination. The method 800 could include further steps, or steps alternative to those listed here.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations wherein embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
an array of antennas, wherein the array of antennas can be mounted proximate a skin surface and to span a specified area of the skin surface when so mounted, such that each antenna of the array of antennas has a respective degree of electromagnetic coupling with an antenna of an implanted device that is implanted beneath the skin surface; and
a controller operably coupled to the array of antennas, wherein the controller comprises a computing device programmed to perform operations comprising:
determining a location, relative to the array of antennas, of the implanted device;
determining, based on the determined location of the implanted device, an amplitude and a relative phase for each of at least two antennas of the array of antennas; and
operating the at least two antennas of the array of antennas to provide electromagnetic energy to the implanted device, wherein operating the at least two antennas comprises emitting from each of the at least two antennas electromagnetic energy according to a corresponding determined amplitude and relative phase.

2. The device of claim 1, wherein the device further comprises a ground plane for the array of antennas, wherein the ground plane is separated from the array of antennas by a spacing layer.

3. The device of claim 1, further comprising a contact layer, wherein the contact layer contacts the skin surface and is disposed between the skin surface and the array of antennas when the array of antennas is mounted proximate the skin surface.

4. The device of claim 1, wherein each antenna of the array of antennas is coupled to the controller via a respective modulator, wherein each modulator is operable to control an amplitude and a relative phase of electromagnetic energy provided, from the controller, to a respective antenna.

5. The device of claim 1, wherein each antenna of the array of antennas has a respective degree of electromagnetic coupling with a further antenna of a further implanted device that is implanted beneath the skin surface, and wherein the operations further comprise:
determining a further location, relative to the array of antennas, of the further implanted device;
wherein determining, based on the determined location of the implanted device, an amplitude and a relative phase for each of the at least two antennas of the array of antennas comprises determining the amplitude and relative phase for each of the at least two antennas of the array of antennas based on the determined location of the implanted device and the determined further location of the further implanted device such that emitting from each of the at least two antennas electromagnetic energy according to a corresponding determined amplitude and relative phase provides electromagnetic energy to both the implanted device and the further implanted device.

6. A device comprising:
an array of antennas, wherein the array of antennas can be mounted proximate a skin surface and to span a specified area of the skin surface when so mounted, such that each antenna of the array of antennas has a respective degree of electromagnetic coupling with an antenna of an implanted device that is implanted beneath the skin surface; and
a controller operably coupled to the array of antennas, wherein the controller comprises a computing device programmed to perform operations comprising:
determining a location, relative to the array of antennas, of the implanted device;
selecting, based on the determined location of the implanted device, two or more antennas of the array of antennas;
determining, based on the determined location of the implanted device, an amplitude and a relative phase for each of the selected two or more antennas; and
operating the selected two or more antennas to provide electromagnetic energy to the implanted device, wherein operating the selected two or more antennas comprises emitting from each of the selected two or more antennas electromagnetic energy according to a corresponding determined amplitude and relative phase.

7. The device of claim 6, wherein at least one antenna of the array of antennas comprises an antenna coil.

8. The device of claim 6, wherein the device further comprises a ground plane for the array of antennas, wherein the ground plane is separated from the array of antennas by a spacing layer.

9. The device of claim 6, further comprising a contact layer, wherein the contact layer contacts the skin surface and is disposed between the skin surface and the array of antennas when the array of antennas is mounted proximate the skin surface.

10. The device of claim 9, wherein the contact layer has a thickness that is between approximately 0.1 millimeters and approximately 0.4 millimeters.

11. The device of claim 6, further comprising:
a radio frequency switch, wherein each antenna of the array of antennas is coupled to the radio frequency switch, wherein operating the selected two or more antennas to provide electromagnetic energy to the implanted device comprises operating the radio frequency switch to couple the selected two or more antennas to the controller.

12. The device of claim 11, wherein each antenna of the array of antennas is coupled to the radio frequency switch via a respective modulator, wherein each modulator is operable to control an amplitude and a relative phase of electromagnetic energy provided, from the radio frequency switch, to a respective antenna.

13. The device of claim 6, wherein determining a location of the implanted device comprises:
for each antenna of the array of antennas, (i) providing electromagnetic energy via the antenna, and (ii) detecting a received signal strength of a radio frequency signal received by the antenna; and
determining a location of an implanted device based on the detected received signal strengths.

14. The device of claim 6, wherein determining a location of the implanted device comprises:
for each antenna of the array of antennas, (i) providing electromagnetic energy via the antenna, and (ii) receiving, from the implanted device, a wireless transmission indicating an amount of electromagnetic energy received, by the implanted device, from the antenna; and
determining a location of an implanted device based on the received wireless transmissions.

15. The device of claim 6, wherein each antenna of the array of antennas has a respective degree of electromagnetic coupling with a further antenna of a further implanted device that is implanted beneath the skin surface, and wherein the operations further comprise:
determining a further location, relative to the array of antennas, of the further implanted device;
wherein selecting, based on the determined location of the implanted device, two or more antennas of the array of antennas comprises selecting two or more antennas of the array of antennas based on the determined location of the implanted device and the determined further location of the further implanted device; and
wherein determining, based on the determined location of the implanted device, an amplitude and a relative phase for each of the selected two or more antennas comprises determining the amplitude and relative phase for each of the selected two or more antennas based on the determined location of the implanted device and the determined further location of the further implanted device such that emitting from each of the selected two or more antennas electromagnetic energy according to a corresponding determined amplitude and relative phase provides electromagnetic energy to both the implanted device and the further implanted device.

16. A method comprising:
determining a location of an implanted device relative to an array of antennas in a reader device mounted to a skin surface, wherein the array of antennas spans a specified area of the skin surface, wherein the implanted device is implanted beneath the skin surface, and wherein each antenna of the array of antennas has a respective degree of electromagnetic coupling with an antenna of the implanted device;
selecting, based on the determined location of the implanted device, two or more antennas of the array of antennas;
determining, based on the determined location of the implanted device, an amplitude and a relative phase for each of the selected two or more antennas; and
providing, via the selected two or more antennas, electromagnetic energy to the implanted device, wherein providing electromagnetic energy to the implanted device comprises emitting from each of the selected two or more antennas electromagnetic energy according to a corresponding determined amplitude and relative phase.

17. The method of claim 16, wherein the reader device further comprises a contact layer, wherein the contact layer contacts the skin surface and is disposed between the skin surface and the array of antennas when the array of antennas is mounted proximate the skin surface.

18. The method of claim 16, wherein determining a location of the implanted device comprises:
for each antenna of the array of antennas, (i) providing electromagnetic energy via the antenna, and (ii) detecting a received signal strength of an electromagnetic signal received by the antenna; and
determining a location of an implanted device based on the detected received signal strengths.

19. The method of claim 16, wherein determining a location of the implanted device comprises:
for each antenna of the array of antennas, (i) providing electromagnetic energy via the antenna, and (ii) receiving, from the implanted device, a wireless transmission indicating an amount of electromagnetic energy received, by the implanted device, from the antenna; and
determining a location of an implanted device based on the received wireless transmissions.

20. The method of claim 16, further comprising:
determining a further location, relative to the array of antennas, of the further implanted device;
wherein selecting, based on the determined location of the implanted device, two or more antennas of the array of antennas comprises selecting two or more antennas of the array of antennas based on the determined location of the implanted device and the determined further location of the further implanted device; and
wherein determining, based on the determined location of the implanted device, an amplitude and a relative phase for each of the selected two or more antennas comprises determining the amplitude and relative phase for each of the selected two or more antennas based on the determined location of the implanted device and the determined further location of the further implanted device such that emitting from each of the selected two or more antennas electromagnetic energy according to a corresponding determined amplitude and relative phase provides electromagnetic energy to both the implanted device and the further implanted device.

* * * * *